(12) United States Patent
Sawabe et al.

(10) Patent No.: US 10,682,323 B2
(45) Date of Patent: Jun. 16, 2020

(54) THERAPEUTIC AGENT FOR GLAUCOMA

(71) Applicant: TOA EIYO LTD., Chuo-ku (JP)

(72) Inventors: Toshihiro Sawabe, Fukushima (JP); Fumito Maruyama, Ota-ku (JP); Akiyuki Takaya, Minato-ku (JP); Takeshi Hasegawa, Date (JP)

(73) Assignee: TOA EIYO LTD., Chuo-ku (JP)

( * ) Notice: Subject to any disclaimer, the term of this patent is extended or adjusted under 35 U.S.C. 154(b) by 0 days.

(21) Appl. No.: 16/317,921

(22) PCT Filed: Jul. 21, 2017

(86) PCT No.: PCT/JP2017/026391
§ 371 (c)(1),
(2) Date: Jan. 15, 2019

(87) PCT Pub. No.: WO2018/016611
PCT Pub. Date: Jan. 25, 2018

(65) Prior Publication Data
US 2019/0231724 A1 Aug. 1, 2019

(30) Foreign Application Priority Data
Jul. 22, 2016 (JP) .................................. 2016-144392

(51) Int. Cl.
| | | |
|---|---|---|
| *C07D 333/20* | (2006.01) | |
| *A61K 31/197* | (2006.01) | |
| *A61P 27/06* | (2006.01) | |
| *C07D 333/16* | (2006.01) | |
| *C07C 229/38* | (2006.01) | |
| *A61K 31/382* | (2006.01) | |
| *C07D 311/68* | (2006.01) | |
| *C07C 255/59* | (2006.01) | |
| *A61K 31/277* | (2006.01) | |
| *A61K 31/343* | (2006.01) | |

(Continued)

(52) U.S. Cl.
CPC .......... *A61K 31/197* (2013.01); *A61K 31/277* (2013.01); *A61K 31/343* (2013.01); *A61K 31/353* (2013.01); *A61K 31/381* (2013.01); *A61K 31/382* (2013.01); *A61P 27/06* (2018.01); *C07C 229/38* (2013.01); *C07C 255/59* (2013.01); *C07D 311/68* (2013.01); *C07D 333/16* (2013.01)

(58) Field of Classification Search
CPC .. A61K 31/197; A61K 31/343; A61K 31/353; A61K 31/381; A61K 31/277; A61K 31/382; A61P 27/06; A61P 27/02; C07C 255/59; C07C 229/38; C07D 311/68; C07D 333/16
USPC ......................................................... 549/75
See application file for complete search history.

(56) References Cited

U.S. PATENT DOCUMENTS

| | | |
|---|---|---|
| 8,981,104 B2 | 3/2015 | Hahn et al. |
| 2015/0119418 A1 | 4/2015 | Uemoto et al. |
| 2015/0148376 A1 | 5/2015 | Hahn et al. |
| 2015/0174113 A1 | 6/2015 | Huebsch et al. |
| 2016/0264514 A1 | 9/2016 | Uemoto et al. |
| 2017/0197940 A1 | 7/2017 | Adams et al. |

(Continued)

FOREIGN PATENT DOCUMENTS

| | | |
|---|---|---|
| JP | 2015-522597 A | 8/2015 |
| JP | 2015-524401 A | 8/2015 |

(Continued)

OTHER PUBLICATIONS

Wikipedia, Partition Coefficient, Mar. 2014, p. 1-11. (Year: 2014).*
International Search Report dated Sep. 19, 2017 in PCT/JP2017/026391 filed on Jul. 21, 2017.

(Continued)

*Primary Examiner* — Taylor V Oh
(74) *Attorney, Agent, or Firm* — Oblon, McClelland, Maier & Neustadt, L.L.P.

(57) ABSTRACT

Provided is a novel therapeutic agent for glaucoma, which has sGC-activating action. A therapeutic agent for glaucoma or an ocular hypotensive agent, which contains, as an effective component, a compound represented by Formula (I-a) or Formula (I-b) and having a Log D value of more than 1.5 and less than 2.5, or a pharmaceutically acceptable salt thereof. [In formulae (I-a) and (I-b), each symbol is as defined in the description.]

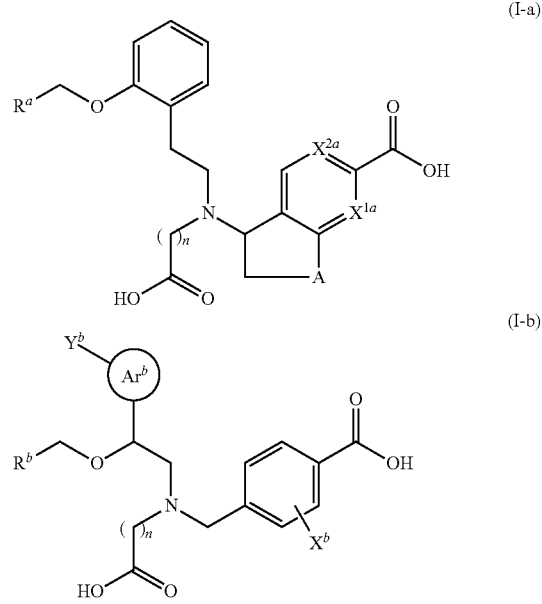

6 Claims, No Drawings

(51) Int. Cl.
    *A61K 31/353*    (2006.01)
    *A61K 31/381*    (2006.01)

(56) References Cited

U.S. PATENT DOCUMENTS

| | | |
|---|---|---|
| 2017/0197941 A1 | 7/2017 | Adams et al. |
| 2017/0197950 A1 | 7/2017 | Adams et al. |

FOREIGN PATENT DOCUMENTS

| | | |
|---|---|---|
| WO | WO 2013/157528 A1 | 10/2013 |
| WO | WO 2015/056663 A1 | 4/2015 |
| WO | WO 2015/095515 A1 | 6/2015 |
| WO | WO 2016/001875 A1 | 1/2016 |
| WO | WO 2016/001876 A1 | 1/2016 |
| WO | WO 2016/001878 A1 | 1/2016 |

OTHER PUBLICATIONS

Schmidt, H. H. H. W., et al. "NO- and Haem-Independent Soluble Guanylate Cyclase Activators", Handbook of Experimental Pharmacology, Germany, Springer-Verlag, 2009, vol. 191, pp. 309-339.
Stasch, J-P. et al., "NO-Independent, Haem-Dependent Soluble Guanylate Cyclase Stimulators", Handbook of Experimental Pharmacology, Germany, Springer-Verlag, 2009, vol. 191, pp. 277-308.
Ellis, D. Z., "Guanylate Cyclase Activators, Cell Volume Changes and IOP Reduction", Cellular Physiology and Biochemistry, Switzerland, S. Karger AG, 2011, vol. 28, pp. 1145-1154.
Stasch, J-P. et al., "Targeting the heme-oxidized nitric oxide receptor for selective vasodilatation of diseased blood vessels", The Journal of Clinical Investigation, U.S.A., American Society for Clinical Investigation, 2006, vol. 116, No. 9, pp. 2552-2561.
Schermuly, R. T. et al., "Expression and function of soluble guanylate cyclase in pulmonary arterial hypertension", European Respiratory Journal, Switzerland, European Respiratory Society, 2008, vol. 32, No. 4, pp. 881-891.

* cited by examiner

THERAPEUTIC AGENT FOR GLAUCOMA

TECHNICAL FIELD

The present invention relates to a therapeutic agent for glaucoma including an sGC activator.

BACKGROUND ART

Glaucoma is a disease in which a disorder of the optic nerve which transmits visual information to the brain causes atrophy of the optic nerve to narrow the visual field. As the type of disease, for example, primary open-angle glaucoma (POAG), normal tension glaucoma, primary angle-closure glaucoma, developmental glaucoma, and secondary glaucoma are known. In addition, ocular hypertension, which is a state that the visual field is normal, but the intraocular pressure is chronically high, is one of the risk factors of glaucoma.

The onset mechanism of primary open-angle glaucoma (POAG) is considered to be that the trabecular meshwork which is an outlet of the aqueous humor is gradually clogged, whereby intraocular pressure (IOP) increases. The normal tension glaucoma is a disease in which although the intraocular pressure is in a normal range (10 to 21 mmHg), glaucoma is developed, and classified into primary open-angle glaucoma. The primary angle-closure glaucoma is a disease in which a corner angle becomes narrow to hinder the flow of the aqueous humor, thereby increasing intraocular pressure.

In the treatment of glaucoma, the first priority is considered to be decreasing intraocular pressure so that no further disturbance of the visual field progresses, and in order to decrease intraocular pressure, medication treatment, laser treatment, or surgical operation is performed. However, not all patients are satisfied with these existing treatments, and there is a need for a new therapeutic agent for glaucoma which contains effective component exhibiting a new mechanism of action or having a new structure unknown for the existing therapeutic agents.

Soluble guanylate cyclase (sGC) is an enzyme which produces cyclic guanosine monophosphate (cGMP) from guanosine triphosphate (GTP), and composed of a dimer of an α subunit and a β subunit. The β subunit is bound to heme, and usually iron coordinated to heme and a histidine residue which is the 105th amino acid interact with each other to take an inactivated structure. Nitrogen monoxide (NO) which is known as a main in vivo activation factor of sGC, interacts with heme iron present in the β subunit of sGC, and dissociates the interaction of the heme iron and the histidine residue of the β subunit, thereby performing transition to an activated structure. cGMP produced by activated sGC activates for example, the protein kinase or ion channel, and performs various roles such as relaxation of vascular smooth muscle inhibition of platelet activation, inhibition of cell growth, or olfactory neurotransmission (Non Patent Literatures 1 and 2).

sGC is also involved in the regulation of intraocular pressure, and Non Patent Literature 3 suggests that the sGC activator reduces a cell volume of the trabecular meshwork or the Schlemm's canal, which is the outlet of the aqueous humor, thereby promoting discharge of the aqueous humor, and representing intraocular pressure lowering. Thus, the sGC activator is expected as a therapeutic agent for glaucoma. Meanwhile, it is considered that in glaucoma, oxidative stress is enhanced, and also under the condition in which oxidative stress is enhanced, oxidation of heme iron or decomposition of heme is enhanced, and thus, as the therapeutic agent for glaucoma, heme-independent sGC activator is preferred (Non Patent Literatures 4 and 5). In addition, degrees of enhancement of oxidative stress are different for each patient, and become a factor of variation in a medicinal effect or side effects, and thus, variation of the activation effect due to the oxidation state of heme iron is preferably small.

Patent Literature 1 discloses that pyrazole carboxylic acid and imidazole carboxylic acid derivatives have a high effect on a monkey ocular hypertension model. However, though it is suggested that these derivatives are heme-independent, the degree of a change in the activation effect depending on the oxidation state of heme iron is not reviewed. In addition, Patent Literature 1 discloses that Cinaciguat which is a representative heme-independent sGC activator, has a low intraocular pressure lowering action.

Meanwhile, as a heme-independent sGC activator, Patent Literature 2 discloses a compound represented by General Formula A:

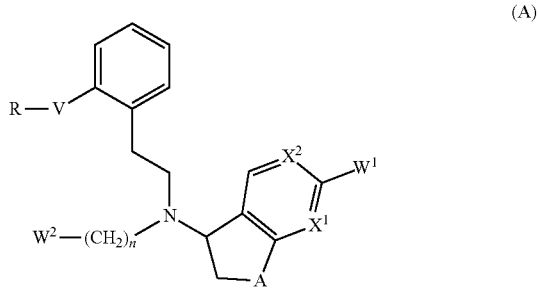

(A)

(for each symbol in the formula, see the publication), and Patent Literature 3 discloses a compound represented by General Formula B:

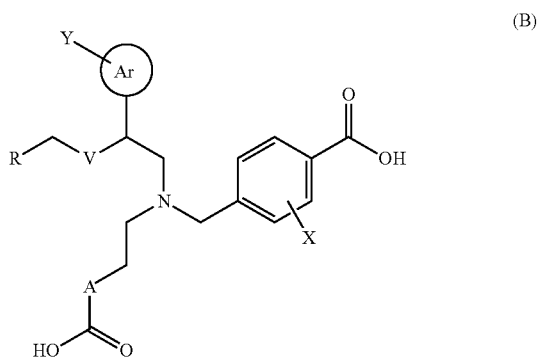

(B)

(for each symbol in the formula, see the publication). It is disclosed that the activity of these compounds is less dependent on the oxidation state of heme iron than that of Cinaciguat; however, the activity of lowering intraocular pressure is not evaluated in the document at all.

CITATION LIST

Patent Literature

Patent Literature 1: WO 2015/095515 A
Patent Literature 2: WO 2013/157528 A
Patent Literature 3: WO 2015/056663 A

3

Non Patent Literature

Non Patent Literature 1: Handbook of Experimental Pharmacology, Germany, Springer-Verlag, 2009, vol. 191, p. 309-339

Non Patent Literature 2: Handbook of Experimental Pharmacology, Germany, Springer-Verlag, 2009, vol. 191, p. 277-308

Non Patent Literature 3: Cellular Physiology and Biochemistry, Switzerland, S. Karger A G, 2011, vol. 28, p. 1145-1154

Non Patent Literature 4: The Journal of Clinical Investigation, U.S.A., American Society for Clinical Investigation, 2006, vol. 116, p. 2552-2561

Non Patent Literature 5: European Respiratory Journal, Switzerland, European Respiratory Society, 2008, vol. 32, p. 881-891

SUMMARY OF INVENTION

Technical Problem

An object of the present invention is to provide a novel therapeutic agent for glaucoma exhibiting sGC activating effect.

Solution to Problem

The present inventor searched the compounds exhibiting an intraocular pressure lowering activity from the compounds exhibiting sGC activating effect, and found that among the compounds described in Patent Literatures 2 and 3, a compound having a certain chemical structure and also a certain range of Log D value is heme-independent, and exhibits an excellent intraocular pressure lowering activity, and thus, is useful as a therapeutic agent for glaucoma, thereby completing the present invention.

Thus, the present invention relates to the following [1] to [5]:

[1] A therapeutic agent for glaucoma or ocular hypotensive agent comprising a compound represented by the following Formula (I-a) or Formula (I-b) having a Log D value of more than 1.5 and less than 2.5, or a pharmaceutically acceptable salt thereof, as an effective component.

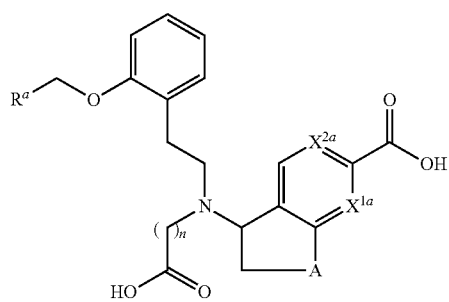

(I-a)

4

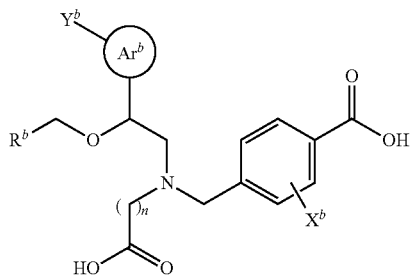

(I-b)

wherein A is a $C_1$-$C_3$ alkylene chain, in which one methylene group is optionally substituted by an oxygen atom or a sulfur atom;

$R^a$ is a group selected from the following formulae:

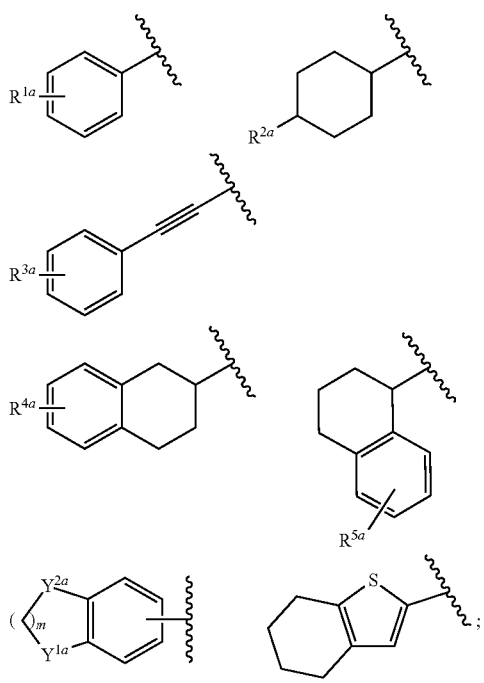

$R^b$ is a group selected from the following formulae:

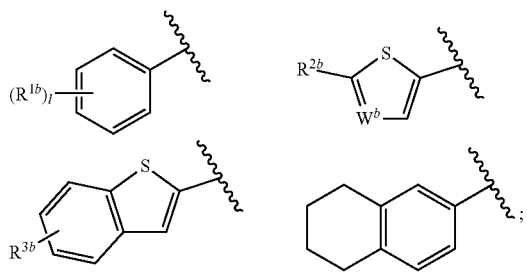

$R^{1a}$, $R^{2a}$, $R^{3a}$, $R^{4a}$, $R^{5a}$, $R^{1b}$, $R^{2b}$, and $R^{3b}$ are a hydrogen atom, a halogen atom, an optionally substituted $C_1$-$C_6$ alkyl group, a $C_1$-$C_6$ alkoxy group, a $C_3$-$C_6$ cycloalkyl group, a $C_3$-$C_6$ cycloalkoxy group, a halo $C_1$-$C_4$ alkyl group, an optionally substituted ethynyl group, an aryl group which is optionally substituted on an aromatic ring, an aryloxy group which is optionally substituted on an aromatic ring, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring;

$Ar^b$ is an aryl group, or a heteroaryl group of a 5- or 6-membered ring containing a nitrogen atom, an oxygen atom, or a sulfur atom;

$X^{1a}$ and $X^{2a}$ are independently from each other CH or a nitrogen atom;

$X^b$ is a hydrogen atom or a halogen atom;

$Y^{1a}$ and $Y^{2a}$ are independently from each other methylene, an oxygen atom, or a sulfur atom, but both of $Y^{1a}$ and $Y^{2a}$ are not a sulfur atom;

$Y^b$ is a hydrogen atom, a $C_1$-$C_6$ alkyl group, a halo $C_1$-$C_4$ alkyl group, a cyano group, or a halogen atom;

$W^b$ is CH or a nitrogen atom;

l is an integer of 1 to 3, and when 1 is 2 or more, $R^{1b}$ may be different from each other;

m is 1 or 2; and n is an integer of 3 to 5.

[2] An ocular hypotensive agent comprising: a compound represented by the above Formula (I-a) or Formula (I-b) having a Log D value of more than 1.5 and less than 2.5, or a pharmaceutically acceptable salt thereof, as an effective component.

[3] Use of a compound represented by the above Formula (I-a) or Formula (I-b) having a Log D value of more than 1.5 and less than 2.5, or a pharmaceutically acceptable salt thereof, for preparing a therapeutic agent for glaucoma or an ocular hypotensive agent.

[4] A compound represented by the above Formula (I-a) or Formula (I-b) having a Log D value of more than 1.5 and less than 2.5, or a pharmaceutically acceptable salt thereof, for treating glaucoma or lowering intraocular pressure.

[5] A method of treating glaucoma or lowering intraocular pressure, comprising administrating an effective amount of a compound represented by the above Formula (I-a) or Formula (I-b) having a Log D value of more than 1.5 and less than 2.5, or a pharmaceutically acceptable salt thereof.

Advantageous Effects of Invention

The compound represented by the above Formula (1-a) or Formula (1-b) having a log D value of more than 1.5 and less than 2.5 or a pharmaceutically acceptable salt thereof which is used in the present invention has an sGC activating effect which is less influenced by the oxidation state of heme iron, and also has an excellent intraocular pressure lowering action, and thus, lowers intraocular pressure in many glaucoma patients, thereby being useful as a therapeutic agent for glaucoma.

DESCRIPTION OF EMBODIMENTS

Hereinafter, the present invention will be described in detail.

In the present specification, a "$C_1$-$C_3$ alkylene chain" refers to a linear alkylene group having 1 to 3 carbon atoms. Specifically, for example, —$CH_2$—, —$(CH_2)_2$—, and —$(CH_2)_3$— are included.

In the present specification, "one methylene group is optionally substituted by an oxygen atom or a sulfur atom" in the "$C_1$-$C_3$ alkylene chain" refers to an optional methylene group in the $C_1$-$C_3$ alkylene chain being substituted by O or S. When the '$C_1$-$C_3$ alkylene chain' is a methylene group having one carbon atom, —O— or —S— is also included. Specifically, for example, —$CH_2O$—, —$CH_2S$—, —$(CH_2)_2S$—, —$(CH_2)_2O$—, and —$CH_2OCH_2$— may be included.

In the present specification, an example of a "halogen atom" may include a fluorine atom, a chlorine atom, a bromine atom, and an iodine atom.

In the present specification, a "$C_1$-$C_6$ alkyl group" refers to a linear chain alkyl group having 1 to 6 carbon atoms or a branched chain alkyl group having 3 to 6 carbon atoms. An example of the $C_1$-$C_6$ alkyl group may include a methyl group, an ethyl group, an n-propyl group, an n-butyl group, an isopropyl group, an isobutyl group, a sec-butyl group, a tert-butyl group, an n-pentyl group, and an n-hexyl group.

In the present specification, a "$C_1$-$C_6$ alkoxy group" refers to a group in which one hydrogen atom of the "$C_1$-$C_6$ alkyl group" is replaced by an oxygen atom. Specifically, the $C_1$-$C_6$ alkoxy group is a linear chain alkoxy group having 1 to 6 carbon atoms or a branched chain alkoxy group having 3 to 6 carbon atoms, and an example thereof may include a methoxy group, an ethoxy group, an n-propoxy group, an isopropoxy group, an n-butoxy group, an isobutoxy group, a tert-butoxy group, an n-pentyloxy group, and an n-hexyloxy group.

In the present specification, a "$C_3$-$C_6$ cycloalkyl group" refers to a cyclic alkyl group having 3 to 6 carbon atoms. Specifically, for example, a cyclopropyl group, a cyclobutyl group, a cyclopentyl group, and a cyclohexyl group may be included.

In the present specification, a "$C_3$-$C_6$ cycloalkoxy group" refers to a group in which one hydrogen atom of the "$C_3$-$C_6$ cycloalkyl group" is replaced by an oxygen atom. Specifically, for example, a cyclopropoxy group, a cyclobutoxy group, a cyclopentyloxy group, and a cyclohexyloxy group may be included.

In the present specification, a "halo $C_1$-$C_4$ alkyl group" refers to a group in which one or more hydrogen atoms of a $C_1$-$C_4$ alkyl group which is a linear chain alkyl group having 1 to 4 carbon atoms or a branched chain alkyl group having 3 or 4 carbon atoms are replaced by a halogen atom. An example of the halo $C_1$-$C_4$ alkyl group may include a chloromethyl group, a dichloromethyl group, a trichloromethyl group, a fluoromethyl group, a difluoromethyl group, a trifluoromethyl group, a bromomethyl group, a dibromomethyl group, a tribromomethyl group, a 2-chloroethyl group, a 2,2-dichloroethyl group, a 2,2,2-trichloroethyl group, a 2-fluoroethyl group, a 2,2-difluoroethyl group, a 2,2,2-trifluoroethyl group, a 1,1,2,2-tetrafluoroethyl group, a pentafluoroethyl group, a 2-bromoethyl group, a 2,2,2-tribromoethyl group, a 3,3,3-trichloropropyl group, a 3,3,3-trifluoropropyl group, a 3,3,3-tribromopropyl group, a 4,4,4-trichlorobutyl group, and a 4,4,4-trifluorobutyl group.

In the present specification, a "halo $C_1$-$C_4$ alkoxy group" refers to a group in which one hydrogen atom of the "halo C1-C4 alkyl group" is replaced by an oxygen atom. An example of the halo $C_1$-$C_4$ alkoxy group may include a chloromethoxy group, a dichloromethoxy group, a trichloromethoxy group, a fluoromethoxy group, a difluoromethoxy group, a trifluoromethoxy group, a 2-chloroethoxy group, a 2,2-dichloroethoxy group, a 2,2,2-trichloroethoxy group, a 2-fluoroethoxy group, a 2,2-difluoroethoxy group, a 2,2,2-trifluoroethoxy group, a 1,1,2,2-tetrafluoroethoxy group, a 1,1,2,2,2-pentafluoroethoxy group, a 3,3,3-trichloropropoxy group, a 3,3,3-trifluoropropoxy group, a 4,4,4-trichlorobutoxy group, and a 4,4,4-trifluorobutoxy group.

In the present specification, an "aryl group" refers to a monocyclic or polycyclic aromatic hydrocarbon group having 6 to 10 carbon atoms. An example of the aryl group may include a phenyl group and a naphthyl group. More specifically, for example, a phenyl group, a 1-naphthyl group, and a 2-naphthyl group may be included.

In the present specification, an "aryloxy group" refers to a group in which one hydrogen atom of the "aryl group" is replaced by an oxygen atom. An example of the aryloxy group may include a phenoxy group and a naphthoxy group. More specifically, for example, a phenoxy group, a 1-naphthoxy group, and a 2-naphthoxy group may be included.

In the present specification, a "heteroaryl group of 5- or 6-membered ring containing a nitrogen atom, an oxygen atom, or a sulfur atom" refers to a monocyclic heteroaryl group having 4 or 5 carbon atoms containing 1 or 2 nitrogen atoms, oxygen atoms or sulfur atoms. Specifically, for example, a furyl group, a thienyl group, a pyrazolyl group, a thiazolyl group, a isothiazolyl group, an oxazolyl group, an isoxazolyl group, an imidazolyl group, a pyrrolyl group, a pyridyl group, a pyridazinyl group, a pyrimidyl group, and a pyrazinyl group.

In the present specification, "optionally substituted" refers to being unsubstituted or having one or more, preferably one or two, and more preferably one identical or different substituent at a substitutable position. An example of the substituent may include a halogen atom, a $C_1$-$C_6$ alkyl group, a $C_1$-$C_6$ alkoxy group, a $C_3$-$C_6$ cycloalkyl group, a $C_3$-$C_6$ cycloalkoxy group, a halo $C_1$-$C_4$ alkyl group, and an aryl group. Each substituent is as defined above, and the groups may be further substituted.

Hereinafter, a preferred embodiment of the compound represented by Formula (I-a) will be described.

A halogen atom represented by $R^{1a}$, $R^{2a}$, $R^{3a}$, $R^{4a}$, and $R^{5a}$ is preferably a fluorine atom or a chlorine atom, and more preferably a fluorine atom.

In a case where an optionally substituted $C_1$-$C_6$ alkyl group represented by $R^{1a}$, $R^{2a}$, $R^{3a}$, $R^{4a}$, and $R^{5a}$ has a substituent, the substituent may be a $C_1$-$C_6$ alkoxy group, a $C_3$-$C_6$ cycloalkyl group, or a $C_3$-$C_6$ cycloalkoxy group, and among them, the $C_3$-$C_6$ cycloalkyl group is preferred, and the cyclohexyl group is particularly preferred. The optionally substituted $C_1$-$C_6$ alkyl group is preferably a methyl group, an ethyl group, an n-propyl group, an isopropyl group, an n-butyl group, a sec-butyl group, an isobutyl group, a tert-butyl group, a 2-methoxyethyl group, a 2-cyclopropylethyl group, or a 2-cyclohexylethyl group, more preferably a methyl group, an ethyl group, an n-propyl group, an isopropyl group, an n-butyl group, a sec-butyl group, an isobutyl group, or a Cert-butyl group, and still more preferably a isopropyl group or a tert-butyl group.

A $C_1$-$C_6$ alkoxy group represented by $R^{1a}$, $R^{2a}$, $R^{3a}$, $R^{4a}$, and $R^{5a}$ is preferably a methoxy group, an ethoxy group, an n-propoxy group, an isopropoxy group, or a tert-butoxy group, and more preferably an isopropoxy group or a tert-butoxy group.

A $C_3$-$C_6$ cycloalkyl group represented by $R^{1a}$, $R^{2a}$, $R^{3a}$, $R^{4a}$, and $R^{5a}$ is preferably a cyclopropyl group, a cyclobutyl group, a cyclopentyl group, or a cyclohexyl group, and more preferably a cyclopropyl group or a cyclobutyl group.

A $C_3$-$C_6$ cycloalkoxy group represented by $R^{1a}$, $R^{2a}$, $R^{3a}$, $R^{4a}$, and $R^{5a}$ may be for example, a cyclopropyloxy group, a cyclopentyloxy group, or a cyclohexyloxy group, and more preferably a cyclopropyloxy group or a cyclohexyloxy group.

A halo $C_1$-$C_4$ alkyl group represented by $R^{1a}$, $R^{2a}$, $R^{3a}$, $R^{4a}$, and $R^{5a}$ is preferably a $C_1$-$C_4$ alkyl group substituted by one or more fluorine atoms, and more preferably a $C_1$-$C_4$ alkyl group substituted by 1 to 5 fluorine atoms. Specifically, a trifluoromethyl group, a 2,2,2-trifluoroethyl group, a 1,1,2,2-tetrafluoroethyl group, or a pentafluoroethyl group may be included, and more preferably a trifluoromethyl group may be included.

In a case where an optionally substituted ethynyl group represented $R^{1a}$, $R^{2a}$, $R^{3a}$, $R^{4a}$, and $R^{5a}$ has a substituent, the substituent is preferably a $C_1$-$C_6$ alkyl group, a $C_3$-$C_6$ cycloalkyl group or an aryl group, and the aryl group is preferably a phenyl group, and the aryl group may be further substituted by for example, a halogen atom, a $C_1$-$C_6$ alkyl group, or a halo $C_1$-$C_4$ alkyl group. The optionally substituted ethynyl group is preferably unsubstituted or preferably has one substituent, and may be for example, a styryl group, an ethynyl group, a 3-methyl-1-butyn-1-yl group, a cyclopropylethynyl group, a cyclohexylethynyl group, or phenylethynyl group, and preferably a 3-methyl-1-butyn-1-yl group, or a cyclopropylethynyl group.

An aromatic ring of an aryl group which is optionally substituted on an aromatic ring, or an aryloxy group which is optionally substituted on an aromatic ring, both of which are represented by $R^{1a}$, $R^{2a}$, $R^{3a}$, $R^{4a}$, and $R^{5a}$, is preferably a benzene ring. In a case where the aromatic ring is substituted, the substituent is preferably a halogen atom, a $C_1$-$C_6$ alkyl group, a $C_1$-$C_6$ alkoxy group, or a halo $C_1$-$C_4$ alkyl group. An optionally substituted aryl group or aryloxy group is preferably unsubstituted or preferably has one or two substituents, and more preferably has one substituent at a para position. The optionally substituted aryl group or aryloxy group may be specifically, for example, a phenyl group, a 4-trifluoromethylphenyl group, a 4-chlorophenyl group, a 4-tert-butylphenyl group, a 4-methoxyphenyl group, a phenoxy group, a 4-trifluoromethylphenoxy group, a 4-chlorophenoxy group, a 4-tert-butylphenoxy group, or a 4-methoxyphenoxy group, preferably a phenyl group, a 4-trifluoromethylphenyl group, a 4-tert-butylphenyl group, a phenoxy group, a 4-trifluoromethylphenoxy group, or a 4-tert-butylphenoxy group and more preferably a phenyl group or a phenoxy group.

It is preferred that a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring, all of which are represented by $R^{1a}$, $R^{2a}$, $R^{3a}$, $R^{4a}$, and $R^{5a}$ (hereinafter, the groups from the benzyl group to the phenyloxymethyl group being collectively referred to as for example, the benzyl group and the like of Formula (I-a)) may be unsubstituted or has one or two substituents on the benzene ring, and it is particularly preferred that the benzyl group and the like of Formula (I-a) have one substituent at a para position. The substituent is preferably a halogen atom, a $C_1$-$C_6$ alkyl group, or a halo $C_3$-$C_4$ alkyl group, more preferably a halo $C_1$-$C_4$ alkyl group, and most preferably a trifluoromethyl group. The benzyl group and the like are preferably a phenethyl group and a benzyloxy group, and particularly preferably a benzyloxy group. The benzyl group and the like of Formula (I-a) which are optionally substituted on a benzene ring, are specifically, for example, a benzyl group, a phenethyl group, a benzyloxy group, a phenyloxymethyl group, a (4-fluoro)phenethyl group, a (4-fluoro)benzyloxy group, a (4-trifluoromethyl)phenethyl group, a (4-trifluoromethyl)benzyloxy group, a (4-tert-butyl) phenethyl group, or a (4-tert-butyl)benzyloxy group, preferably, a phenethyl group, a benzyloxy group, or a phenyloxymethyl group, and more preferably a benzyloxy group or a phenyloxymethyl group.

n is most preferably 4.

$X^{1a}$ and $X^{2a}$ are most preferably CH.

When a group represented by $R^a$ is the following formula:

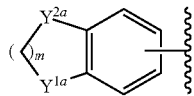

wherein m is an integer of 1 or 2, and $Y^{1a}$ and $Y^{2a}$ are independently from each other a methylene group, O, or S, but both of $Y^{1a}$ and $Y^{2a}$ are not S;

specifically the groups represented by the following formulae may be included:

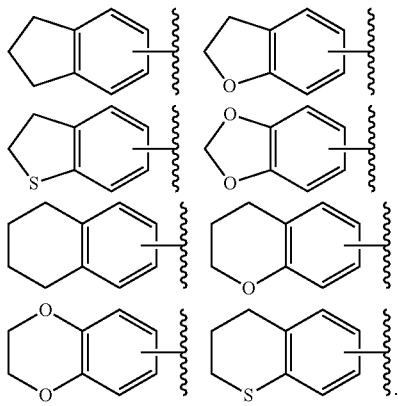

Among them, the groups selected from the following formulae are preferred:

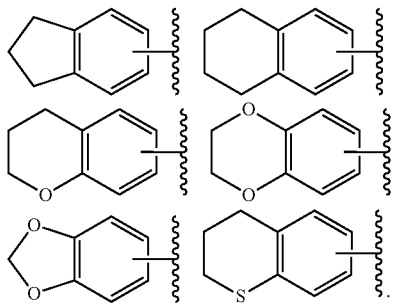

The group represented by $R^a$ is preferably the group selected from the following formulae:

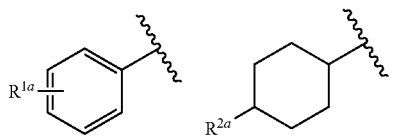

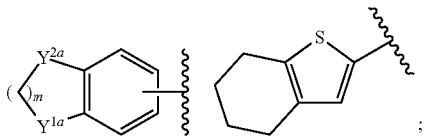

and the group selected from the following formulae:

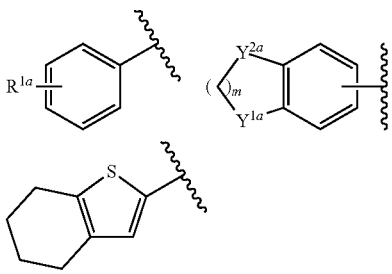

is particularly preferred.

$R^{1a}$ is preferably an optionally substituted $C_1$-$C_6$ alkyl group, a $C_3$-$C_6$ cycloalkyl group, a $C_1$-$C_6$ alkoxy group, a halo $C_1$-$C_4$ alkyl group, an optionally substituted ethynyl group, an aryl group which is optionally substituted on an aromatic ring, an aryloxy group which is optionally substituted on an aromatic ring, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring. More preferably, $R^{1a}$ is an optionally substituted $C_1$-$C_6$ alkyl group, an optionally substituted ethynyl group, a benzyloxy group which is optionally substituted on a benzene ring, or a phenyloxymethyl group which is optionally substituted on a benzene ring. The substitution position of $R^{1a}$ is preferably a meta position or a para position. Here, the substituent on the $C_1$-$C_6$ alkyl group is preferably a $C_1$-$C_6$ alkoxy group, a $C_3$-$C_6$ cycloalkyl group, or a $C_3$-$C_6$ cycloalkoxy group. The substituent on the vinyl group or the ethynyl group is preferably a $C_1$-$C_6$ alkyl group, a $C_3$-$C_6$ cycloalkyl group, a phenyl group, a halogenophenyl group, a $C_1$-$C_6$ alkylphenyl group, or a halo $C_1$-$C_4$ alkylphenyl group. The aryl group is preferably a phenyl group, the aryloxy group is preferably a phenoxy group, and the substituent on the aryl group or the aryloxy group is preferably a halogen atom, a $C_1$-$C_6$ alkyl group, a $C_1$-$C_6$ alkoxy group, or a halo $C_1$-$C_4$ alkyl group. The substituent on the benzene ring is preferably a halogen atom, a $C_1$-$C_6$ alkyl group, or a halo $C_1$-$C_4$ alkyl group.

$R^{2a}$ is preferably an optionally substituted ethynyl group, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring, and more preferably a phenethyl group which is optionally substituted on a benzene ring, or a benzyloxy group which is optionally substituted on a benzene ring. A phenethyl group which is optionally substituted on a benzene ring is most preferred. Here, the substituent on the ethynyl group is preferably a $C_1$-$C_6$ alkyl group, a $C_3$-$C_6$ cycloalkyl group, a phenyl group, a halogenophenyl group, a $C_1$-$C_6$ alkylphenyl group, or a halo $C_1$-$C_4$ alkylphenyl group. The substituent on the benzene ring is preferably a halogen atom, a $C_1$-$C_6$ alkyl group, or a halo $C_1$-$C_4$ alkyl group.

$R^{3a}$ is preferably a hydrogen atom, an optionally substituted $C_1$-$C_6$ alkyl group, a $C_1$-$C_6$ alkoxy group, or a halo $C_1$-$C_4$ alkyl group. A hydrogen atom is most preferred. The substitution position of $R^{3a}$ is most preferably a para position. Here, the substituent on the $C_1$-$C_6$ alkyl group is preferably a $C_1$-$C_6$ alkoxy group, a $C_3$-$C_6$ cycloalkyl group, or a $C_3$-$C_6$ cycloalkoxy group.

$R^{4a}$ is preferably a hydrogen atom, an optionally substituted $C_1$-$C_6$ alkyl group, a $C_1$-$C_6$ alkoxy group, a halo $C_1$-$C_4$ alkyl group, an aryl group which is optionally substituted on an aromatic ring, or an aryloxy group which is optionally substituted on an aromatic ring. A hydrogen atom is most preferred. The substitution position of $R^{4a}$ is preferably a 6-position. Here, the substituent on the $C_1$-$C_6$ alkyl group is preferably a $C_1$-$C_6$ alkoxy group, a $C_3$-$C_6$ cycloalkyl group, or a $C_3$-$C_6$ cycloalkoxy group. The aryl group is preferably a phenyl group, the aryloxy group is preferably a phenoxy group, and the substituent on the aryl group or the aryloxy group is preferably a halogen atom, a $C_1$-$C_6$ alkyl group, a $C_1$-$C_6$ alkoxy group, or a halo $C_1$-$C_4$ alkyl group.

$R^{5a}$ is preferably a hydrogen atom, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring, and a hydrogen atom and a phenethyl group is more preferred. The substitution position of $R^{5a}$ is preferably 6-position. Here, the substituent on the benzene ring is preferably a halogen atom, a $C_1$-$C_6$ alkyl group, or a halo $C_1$-$C_4$ alkyl group.

In General Formula (I-a), it is preferred that A is a methylene group, —O—, —CH$_2$CH$_2$—, —CH$_2$O—, —OCH$_2$—, —CH$_2$CH$_2$CH$_2$—, —CH$_2$OCH$_2$—, —CH$_2$SCH$_2$—, or —CH$_2$CH$_2$O—;
n is an integer of 3 to 5; and
$R^a$ is:

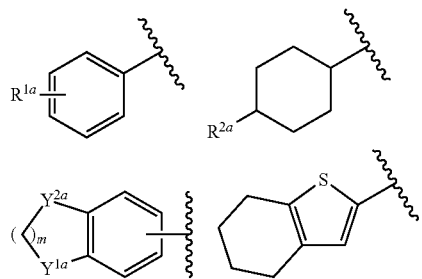

Here, $R^{1a}$, $R^{2a}$, $Y^{1a}$, $Y^{2a}$, and m are as defined above.

In General Formula (I-a), it is more preferred that A is a methylene group, —O—, —CH$_2$CH$_2$—, —CH$_2$O—, —OCH$_2$—, —CH$_2$CH$_2$CH$_2$—, —CH$_2$OCH$_2$—, —CH$_2$SCH$_2$—, or —CH$_2$CH$_2$O—;
n is 4;
$R^a$ is:

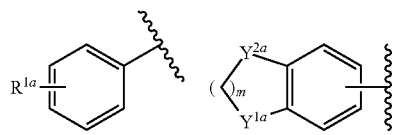

-continued

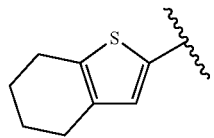

Here, $R^{1a}$, $R^{2a}$, $y^{1a}$, $Y^{2a}$, and m are as defined above.

In the preferred embodiment, $R^{1a}$ is preferably an optionally substituted $C_1$-$C_6$ alkyl group, a $C_3$-$C_6$ cycloalkyl group, a $C_1$-$C_6$ alkoxy group, a halo $C_1$-$C_4$ alkyl group, an optionally substituted ethynyl group, an aryl group which is optionally substituted on an aromatic ring, an aryloxy group which is optionally substituted on an aromatic ring, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring. An optionally substituted $C_1$-$C_6$ alkyl group, an optionally substituted ethynyl group, a benzyloxy group which is optionally substituted on a benzene ring, or a phenyloxymethyl group which is optionally substituted on a benzene ring is more preferred. Here, the substituent on the alkyl group, the ethynyl group, the aryl group, the aryloxy group, and the benzene ring is preferably as defined above.

$R^{2a}$ is preferably an optionally substituted ethynyl group, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring, and a phenethyl group which is optionally substituted on a benzene ring, or a benzyloxy group which is optionally substituted on a benzene ring is more preferred. A phenethyl group which is optionally substituted on a benzene ring is most preferred. Here, the substituent on the ethynyl group and the benzene ring is preferably as defined above.

In the preferred embodiment, when $R^a$ is:

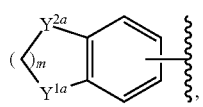

$R^a$ is preferably a group selected from the following:

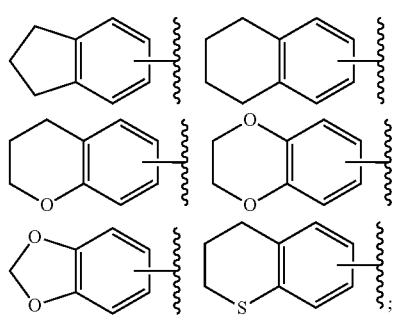

and most preferably the following:

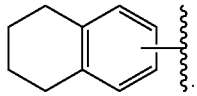

Another preferred embodiment of the compound of Formula (I-a) as the effective component of the medicament of the present invention is shown below.

A compound represented by Formula (I-c) is preferred:

(I-c)

wherein $X^c$ is a methylene group, a single bond or an oxygen atom, and preferably a methylene group; and $R^c$ is a group represented by the following formulae:

Preferably, $R^c$ is a group represented by the following formulae:

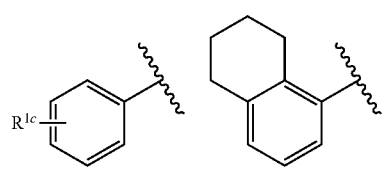 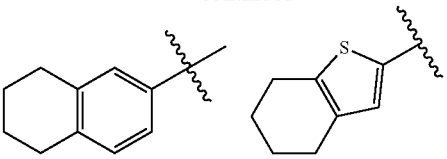

$R^{1c}$ is a hydrogen atom, a halogen atom, an optionally substituted $C_1$-$C_6$ alkyl group, a $C_1$-$C_6$ alkoxy group, a $C_3$-$C_6$ cycloalkyl group, a $C_3$-$C_6$ cycloalkoxy group, a halo $C_3$-$C_4$ alkyl group, an optionally substituted ethynyl group, an aryl group which is optionally substituted on an aromatic ring, an aryloxy group which is optionally substituted on an aromatic ring, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring.

$R^{1c}$ is preferably an optionally substituted $C_1$-$C_6$ alkyl group, an optionally substituted ethynyl group, a phenethyl group which is optionally substituted on a benzene ring, a benzyloxy group which is optionally substituted on a benzene ring, or a phenyloxymethyl group which is optionally substituted on a benzene ring. Among them, an optionally substituted $C_1$-$C_6$ alkyl group, an optionally substituted ethynyl group, a benzyloxy group which is optionally substituted on a benzene ring, or a phenyloxymethyl group which is optionally substituted on a benzene ring is preferred.

The halogen atom represented by $R^{1c}$ is preferably a fluorine atom or a chlorine atom, and a fluorine atom is more preferred.

The optionally substituted $C_1$-$C_6$ alkyl group represented by $R^{1c}$ is preferably an unsubstituted $C_1$-$C_6$ alkyl group, and more preferably a methyl group, an ethyl group, an n-propyl group, an isopropyl group, an n-butyl group, a sec-butyl group, an isobutyl group, or a tert-butyl group, and among them, an isopropyl group, or a tert-butyl group is particularly preferred.

The $C_1$-$C_6$ alkoxy group represented by $R^{1c}$ is preferably a methoxy group, an ethoxy group, an n-propoxy group, an isopropoxy group, or a tert-butoxy group, and more preferably an isopropoxy group and a tert-butoxy group.

The $C_3$-$C_6$ cycloalkoxy group represented by $R^{1c}$ is preferably a cyclopropyloxy group, a cyclopentyloxy group, or a cyclohexyloxy group, and more preferably a cyclopropyloxy group.

The $C_3$-$C_6$ cycloalkyl group represented by $R^{1c}$ is preferably a cyclopropyl group, a cyclobutyl group, or a cyclopentyl group, and among them, a cyclopropyl group is more preferred.

The halo $C_1$-$C_4$ alkyl group represented by $R^{1c}$ is preferably a $C_1$-$C_4$ alkyl group substituted by one or more fluorine atoms, and among them, a $C_1$-$C_4$ alkyl group substituted by 1 to 5 fluorine atoms is more preferred. Specifically, for example, a trifluoromethyl group, a 2,2,2-trifluoroethyl group, a 1,1,2,2-tetrafluoroethyl group, or a pentafluoroethyl group may be included, and among them, a trifluoromethyl group is particularly preferred.

When the optionally substituted ethynyl group represented by $R^{1c}$ is substituted, the substituent is preferably a $C_1$-$C_6$ alkyl group, a $C_3$-$C_6$ cycloalkyl group, or an aryl group, and the aryl group is preferably a phenyl group, and the aryl group may be further substituted by for example, a halogen atom, a $C_1$-$C_6$ alkyl group or a halo $C_1$-$C_4$ alkyl group. The optionally substituted ethynyl group is preferably unsubstituted or preferably has one substituent, and may be for example, a styryl group, an ethynyl group, a 3-methyl-1-butyn-1-yl group, a cyclopropylethynyl group, a cyclohexylethynyl group, or a phenylethynyl group, and a 3-methyl-1-butyn-1-yl group, or a cyclopropylethynyl group is preferred.

The aromatic ring of the aryl group which is optionally substituted on an aromatic ring, or the aryloxy group which is optionally substituted on an aromatic ring, both of which are represented by $R^{1c}$, is preferably a benzene ring. When the aromatic ring is substituted, the substituent is preferably a halogen atom, a $C_1$-$C_6$ alkyl group, a $C_1$-$C_6$ alkoxy group, or a halo $C_1$-$C_4$ alkyl group. The optionally substituted aryl group or aryloxy group is preferably unsubstituted or preferably has one or two substituents, and more preferably has one substituent at a para position. The optionally substituted aryl group or aryloxy group may be specifically, for example, a phenyl group, a 4-trifluoromethylphenyl group, a 4-chlorophenyl group, a 4-tert-butylphenyl group, a 4-methoxyphenyl group, a phenoxy group, a 4-trifluoromethylphenoxy group, a 4-chlorophenoxy group, a 4-tert-butylphenoxy group, or a 4-methoxyphenoxy group, and preferably a phenyl group, a 4-trifluoromethylphenyl group, a 4-tert-butylphenyl group, a phenoxy group, a 4-trifluoromethylphenoxy group, or a 4-tert-butylphenoxy group, and most preferably a phenyl group, or a phenoxy group.

The benzyl group which is optionally substituted on a benzene ring, the phenethyl group which is optionally substituted on a benzene ring, the benzyloxy group which is optionally substituted on a benzene ring, or the phenyloxymethyl group which is optionally substituted on a benzene ring, all of which are represented by $R^{1c}$ (hereinafter, the groups from the benzyl group to the phenyloxymethyl group being collectively referred to as the benzyl group and the like of Formula (I-c)), is preferably unsubstituted or preferably has one or two substituents on the benzene ring, and particularly preferably has one substituent at a para position. The substituent is preferably a halogen atom, a $C_1$-$C_6$ alkyl group, or a halo $C_1$-$C_4$ alkyl group, and more preferably a halo $C_1$-$C_4$ alkyl group, and most preferably a trifluoromethyl group. The benzyl group and the like are preferably a phenethyl group, or a benzyloxy group, and particularly preferably a benzyloxy group. The benzyl group which is optionally substituted on the benzene ring and the like of Formula (I-c), is specifically, for example, a benzyl group, a phenethyl group, a benzyloxy group, a phenyloxymethyl group, a (4-fluoro)phenethyl group, a (4-fluoro)benzyloxy group, a (4-trifluoromethyl)phenethyl group, a (4-trifluoromethyl)benzyloxy group, (4-tert-butyl)phenethyl group, or a (4-tert-butyl)benzyloxy group, and preferably a phenethyl group, a benzyloxy group, or a phenyloxymethyl group, and more preferably a benzyloxy group or a phenyloxymethyl group.

Next, a preferred embodiment of the compound represented by Formula (I-b) will be described.

The halogen atom represented by $R^{1b}$, $R^{2b}$, and $R^{3b}$ is preferably a fluorine atom or a chlorine atom.

When the optionally substituted $C_1$-$C_6$ alkyl group represented by $R^{1b}$, $R^{2b}$, and $R^{3b}$ is substituted, the substituent may be a $C_1$-$C_6$ alkoxy group, a $C_3$-$C_6$ cycloalkyl group, or a $C_3$-$C_6$ cycloalkoxy group, and among them, a $C_3$-$C_6$ cycloalkyl group is preferred, and a cyclopentyl group or a cyclohexyl group is particularly preferred. The optionally substituted $C_1$-$C_G$ alkyl group is preferably a methyl group, an ethyl group, an n-propyl group, an isopropyl group, an n-butyl group, a sec-butyl group, an isobutyl group, a tert-butyl group, a 3,3-dimethylbutyl group, a 2-cyclopentylethyl group, or a 2-cyclohexylethyl group, more preferably a methyl group, an ethyl group, an n-propyl group, an isopropyl group, an n-butyl group, a sec-butyl group, an isobutyl group, or a tert-butyl group, still more preferably isopropyl group or tert-butyl group, and particularly preferably a tert-butyl group.

The $C_3$-$C_6$ cycloalkyl group represented by $R^{1b}$, $R^{2b}$, and $R^{3b}$ is preferably a cyclopropyl group, a cyclobutyl group, a cyclopentyl group, or a cyclohexyl group, and among them, a cyclopropyl group is more preferred.

The $C_3$-$C_6$ cycloalkoxy group represented by $R^{1b}$, $R^{2b}$, and $R^{3b}$ may be a cyclopropyloxy group, a cyclopentyloxy group, or a cyclohexyloxy group, and more preferably a cyclopropyloxy group.

The halo $C_1$-$C_4$ alkyl group represented by $R^{1b}$, $R^{2b}$, and $R^{3b}$ is preferably a $C_1$-$C_4$ alkyl group substituted by one or more fluorine atoms, and among them, a $C_1$-$C_4$ alkyl group substituted by 1 to 5 fluorine atoms are more preferred. Specifically, for example, a trifluoromethyl group, a 2,2,2-trifluoroethyl group, a 1,1,2,2-tetrafluoroethyl group, or a pentafluoroethyl group may be included, and among them, a trifluoromethyl group is particularly preferred.

When the optionally substituted ethynyl group represented by $R^{1b}$, $R^{2b}$, and $R^{3b}$ is substituted, the substituent is preferably a $C_1$-$C_6$ alkyl group, a $C_3$-$C_6$ cycloalkyl group or an aryl group, and the aryl group is preferably a phenyl group, and the aryl group may be further substituted by for example, a halogen atom, a $C_1$-$C_6$ alkyl group or a halo $C_1$-$C_4$ alkyl group. The optionally substituted ethynyl group is preferably unsubstituted or preferably has one substituent, and for example, may be a styryl group, an ethynyl group, a 3-methyl-1-butyn-1-yl group, a cyclopropylethynyl group, a cyclohexylethynyl group, or a phenylethynyl group, and preferably a 3-methyl-1-butyn-1-yl group or a cyclopropylethynyl group.

The aromatic ring of the aryl group which is optionally substituted on an aromatic ring, or the aryloxy group which is optionally substituted on an aromatic ring, both of which are represented by $R^{1b}$, $R^{2b}$ and $R^{3b}$, is preferably a benzene ring. When the aromatic ring is substituted, the substituent is preferably a halogen atom, a $C_1$-$C_6$ alkyl group, a $C_1$-$C_6$ alkoxy group, or a halo $C_1$-$C_4$ alkyl group. The optionally substituted aryl group or aryloxy group is preferably unsubstituted or preferably has one or two substituents, and more preferably has one substituent at a para position. The optionally substituted aryl group or aryloxy group may be specifically, for example, a phenyl group, a 4-trifluoromethylphenyl group, a 4-chlorophenyl group, a 4-tert-butylphenyl group, a 4-methoxyphenyl group, a phenoxy group, a 4-trifluoromethylphenoxy group, a 4-chlorophenoxy group, a 4-tert-butylphenoxy group, or a 4-methoxyphenoxy group, preferably a phenyl group, a 4-trifluoromethylphenyl group, a 4-tert-butylphenyl group, a phenoxy group, a 4-trifluoromethylphenoxy group, a 4-chlorophenoxy group, or a 4-tert-butylphenoxy group, and more preferably a phenyl group, a phenoxy group, or a 4-chlorophenoxy group The benzyl group which is optionally substituted on a benzene ring, the phenethyl group which is optionally substituted on a benzene ring, the benzyloxy group which is optionally substituted on a benzene ring, or the phenyloxymethyl group which is optionally substituted on a benzene ring, all of which are represented by $R^{1b}$, $R^{2b}$, and $R^{3b}$ (hereinafter, the groups from the benzyl group to the phenyloxymethyl group being collectively referred to as the benzyl group and the like of Formula (I-b)) is preferably unsubstituted or preferably has one or two substituents on a benzene ring, and among them, having one substituent at a para position is particularly preferred. The substituent is preferably a halogen atom, a $C_1$-$C_6$ alkyl group, or a halo $C_1$-$C_4$ alkyl group, and among them, a chlorine atom, or a trifluoromethyl group is more preferred, and a chlorine atom is still more preferred. The benzyl group and the like of Formula (I-b) are preferably a phenethyl group or a benzyloxy group, and more preferably a phenethyl group. The benzyl group and the like which are optionally substituted on a benzene ring may be specifically, for example, a benzyl group, a phenethyl group, a benzyloxy group, a phenyloxymethyl group, a (4-fluoro)phenethyl group, a (4-chloro)phenethyl group, a (4-fluoro)benzyloxy group, a (4-trifluoromethyl)phenethyl group, a (4-trifluoromethyl)benzyloxy group, a (4-tert-butyl)phenethyl group, or a (4-tert-butyl)benzyloxy group, preferably a phenethyl group, a benzyloxy group, a phenyloxymethyl group, or a (4-chloro)phenethyl group, more preferably a phenethyl group, a benzyloxy group, or a (4-chloro)phenethyl group, and still more preferably a phenethyl group or a (4-chloro)phenethyl group.

The $C_6$-$C_{10}$ aryl group or heteroaryl group of 5- or 6-membered ring containing a nitrogen atom, an oxygen atom, or a sulfur atom represented by $Ar^b$ may be specifically, for example, a phenyl group, a furyl group, a thienyl group, a thiazolyl group, an oxazolyl group, an imidazolyl group, a pyrrolyl group, a pyridyl group, or a pyrimidyl group, and among them, a phenyl group or a thienyl group is preferred.

$Y^b$ is a hydrogen atom, a $C_1$-$C_6$ alkyl group, a halo $C_1$-$C_4$ alkyl group, a cyano group, or a halogen atom.

The $C_1$-$C_6$ alkyl group represented by $Y^b$ may be specifically, for example, a methyl group, an ethyl group, an n-propyl group, an n-butyl group, an isopropyl group, an isobutyl group, a sec-butyl group, a tert-butyl group, or a 2,2-dimethylpropyl group. Among them, a methyl group or an ethyl group is preferred, and a methyl group is most preferred.

The halo $C_1$-$C_4$ alkyl group represented by $Y^b$ is preferably a fluoromethyl group, a difluoromethyl group, a trifluoromethyl group, or a pentafluoroethyl group.

The halogen atom represented by $Y^b$ may be specifically, for example, a fluorine atom, a chlorine atom, a bromine atom, or an iodine atom. Among them, a chlorine atom or a fluorine atom is preferred, and a fluorine atom is particularly preferred.

$Y^b$ is particularly preferably a methyl group, a cyano group, or a fluorine atom. When $Ar^b$ is a 6-membered ring, the substitution position of $Y^b$ to $Ar^b$ is preferably a meta position or a para position, and most preferably a meta position. When $Ar^b$ is a heteroaryl group, the substitution position of $Y^b$ to $Ar^b$ is preferably a carbon atom adjacent to a hetero atom.

$X^b$ is a hydrogen atom or a halogen atom. Among them, $X^b$ is preferably a hydrogen atom or a fluorine atom. The substitution position of $X^b$ is preferably an ortho position to a carboxyl group.

When the group represented by $R^b$ is the following formula:

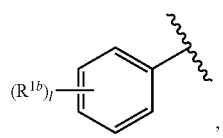

l is particularly preferably 1 or 2.

The group represented by $R^b$ is the following formula:

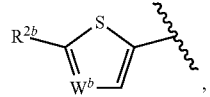

wherein $W^b$ is CH or a nitrogen atom, and among them, preferably CH.

The group represented by $R^b$ is preferably a group selected from the following formulae:

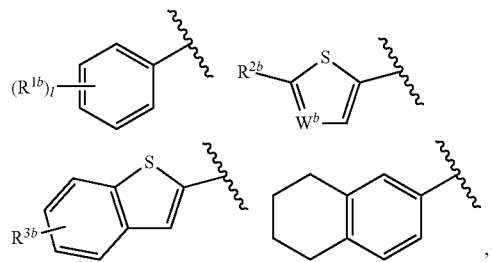

and among them, the following formulae:

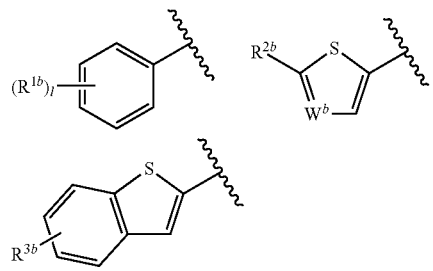

are particularly preferred.

$R^{1b}$ is preferably a halogen atom, an optionally substituted $C_1$-$C_6$ alkyl group, a halo $C_1$-$C_4$ alkyl group, an aryl group which is optionally substituted on an aromatic ring, an aryloxy group which is optionally substituted on an aromatic ring, or the benzyl group and the like of Formula (I-b) which are optionally substituted on a benzene ring. Among them, an optionally substituted $C_1$-$C_6$ alkyl group, a phenethyl group which is optionally substituted on a benzene ring or a benzyloxy group is more preferred. The substitution position of $R^{1b}$ is preferably a meta position or a para position. In addition, when n is 2, a combination of an ortho position and a para position or a combination of meta positions is preferred. Here, the substituent on the $C_1$-$C_6$ alkyl group is preferably a $C_3$-$C_6$ cycloalkyl group. The aryl group is preferably a phenyl group, the aryloxy group is preferably a phenoxy group, and the substituent on the aryl group or the aryloxy group is preferably a halogen atom, a $C_1$-$C_6$ alkyl group, a halo $C_1$-$C_4$ alkyl group or a cyano group. The substituent on the benzene ring is preferably a halogen atom or a halo $C_1$-$C_4$ alkyl group.

$R^{2b}$ is preferably an optionally substituted $C_1$-$C_6$ alkyl group, an aryl group which is optionally substituted on an aromatic ring, an aryloxy group which is optionally substituted on an aromatic ring, or a phenethyl group which is optionally substituted on a benzene ring. Among them, a phenethyl group which is optionally substituted on a benzene ring is most preferred. Here, the $C_1$-$C_6$ alkyl group is preferably unsubstituted. The aryl group is preferably a phenyl group, and the aryloxy group is preferably a phenoxy group, and it is preferred that the aryl group or the phenethyl group is unsubstituted, and the aryloxy group is substituted by a $C_1$-$C_6$ alkyl group.

$R^{3b}$ is preferably a halogen atom, an optionally substituted $C_1$-$C_6$ alkyl group, or a $C_3$-$C_6$ cycloalkyl group. The substitution position of $R^{3b}$ is most preferably a 6-position. Here, the $C_1$-$C_6$ alkyl group or the $C_3$-$C_6$ cycloalkyl group is preferably unsubstituted.

n is most preferably 4.

In General Formula (I-b), it is preferred that $Ar^b$ is a phenyl group or a thienyl group;
$X^b$ is a hydrogen atom or a halogen atom;
$Y^b$ is a hydrogen atom, a $C_1$-$C_6$ alkyl group, a cyano group, or a halogen atom;
n is an integer of 3 to 5; and
$R^b$ is the following Formulae:

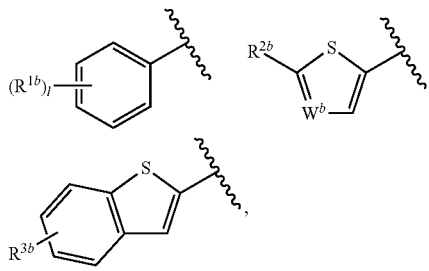

wherein $R^{1b}$, $R^{2b}$, $R^{3b}$, $W^b$, and l are as defined above.

In General Formula (I-b), it is preferred that $Ar^b$ is a phenyl group or a thienyl group;
$X^b$ is a hydrogen atom or a halogen atom;
$Y^b$ is a hydrogen atom, a $C_1$-$C_6$ alkyl group, a cyano group, or a halogen atom;
n is 4; and
$R^b$ is the following formulae:

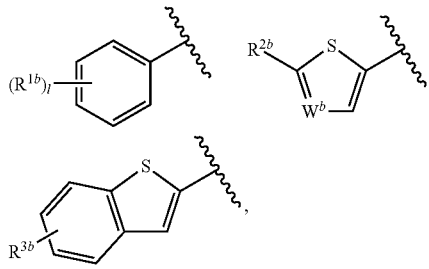

wherein, $R^{1b}$, $R^{2b}$, $R^{3b}$, $W^b$, and l are as defined above.

In the preferred embodiment, $R^{1b}$ is preferably a halogen atom, an optionally substituted $C_1$-$C_6$ alkyl group, a halo $C_1$-$C_4$ alkyl group, an aryloxy group which is optionally substituted on an aromatic ring, a phenethyl group which is optionally substituted on a benzene ring, or a benzyloxy group which is optionally substituted on a benzene ring. Among them, an optionally substituted $C_1$-$C_6$ alkyl group, a phenethyl group which is optionally substituted on a benzene ring, or a benzyloxy group which is optionally substituted on a benzene ring is more preferred, and a phenethyl group which is optionally substituted on a benzene ring is still more preferred. Here, it is preferred that the substituent on the alkyl group, the aryloxy group and the benzene ring is the same as the above.

$R^{2b}$ is preferably an optionally substituted $C_1$-$C_6$ alkyl group, an aryl group which is optionally substituted on an aromatic ring, an aryloxy group which is optionally substituted on an aromatic ring, or a phenethyl group which is optionally substituted on a benzene ring. Among them, a phenethyl group which is optionally substituted on a benzene ring is most preferred. Here, it is preferred that the substituent on the alkyl group, the aryl group, the aryloxy group and the benzene ring is the same as the above.

$R^{2b}$ is preferably a halogen atom, an optionally substituted $C_1$-$C_6$ alkyl group, or a $C_3$-$C_6$ cycloalkyl group. Here, it is preferred that the substituent of the alkyl group is the same as the above.

Another preferred embodiment of the compound of Formula (I-b) as an effective component of the medicament of the present invention will be described below.

The compound represented by Formula (I-d) is preferred:

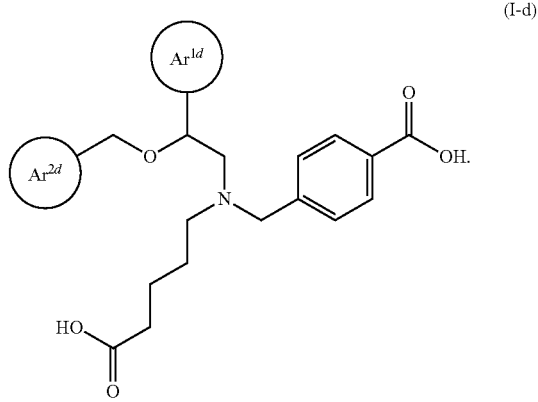

In Formula (I-d), $Ar^{1d}$ is a group represented by the following formulae:

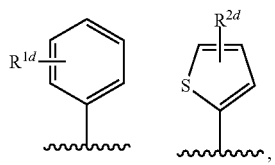

and preferably, a group represented by the following formulae:

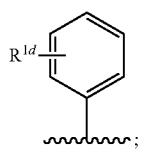

and
$Ar^{2d}$ is a group represented by the following formulae:

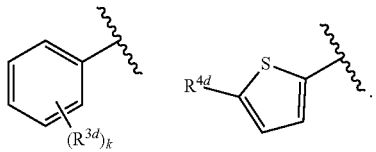

and
preferably, a group represented by the following formulae:

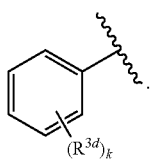

$R^{1d}$ and $R^{2d}$ are a hydrogen atom, a $C_1$-$C_6$ alkyl group, a halo $C_1$-$C_4$ alkyl group, a cyano group, or a halogen atom.

$R^{1d}$ and $R^{2d}$ are preferably a hydrogen atom, a $C_1$-$C_6$ alkyl group, a cyano group, or a halogen atom, more preferably a hydrogen atom, a cyano group, or a halogen atom, and still more preferably a hydrogen atom, or a halogen atom.

Here, the $C_1$-$C_6$ alkyl group represented by $R^{1d}$ and $R^{2d}$ is preferably a methyl group, an ethyl group, an n-propyl group, or an isopropyl group, more preferably a methyl group or an ethyl group, and still more preferably a methyl group.

The halo $C_1$-$C_4$ alkyl group represented by $R^{1d}$ and $R^{2d}$ is preferably a $C_1$-$C_4$ alkyl group substituted by one or more fluorine atoms, and among them, a $C_1$-$C_4$ alkyl group substituted by 1 to 5 fluorine atoms is more preferred. Specifically, for example, a fluoromethyl group, a difluoromethyl group, a trifluoromethyl group, or a pentafluoroethyl group may be included, and a trifluoromethyl group is preferred.

The halogen atom represented by $R^{1d}$ and $R^{2d}$ may be a fluorine atom, a chlorine atom, a bromine atom, or an iodine atom, preferably a fluorine atom, a chlorine atom, or a bromine atom, more preferably a fluorine atom or a chlorine atom, and still more preferably a fluorine atom.

$R^{3d}$ and $R^{4d}$ are a hydrogen atom, a halogen atom, an optionally substituted $C_1$-$C_6$ alkyl group, a $C_1$-$C_6$ alkoxy group, a $C_3$-$C_6$ cycloalkyl group, a $C_3$-$C_6$ cycloalkoxy group, a halo $C_1$-$C_4$ alkyl group, an optionally substituted ethynyl group, an aryl group which is optionally substituted on an aromatic ring, an aryloxy group which is optionally substituted on an aromatic ring, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring. However, when $R^{1d}$ or $R^{2d}$ is a cyano group, $R^{3d}$ is not an aryloxy group which is optionally substituted on an aromatic ring.

$R^{3d}$ and $R^{4d}$ is preferably an optionally substituted $C_1$-$C_6$ alkyl group, an aryloxy group which is optionally substituted on an aromatic ring, a phenethyl group which is optionally substituted on a benzene ring, a benzyloxy group which is optionally substituted on a benzene ring, or a phenyloxymethyl group which is optionally substituted on a benzene ring. Among them, an optionally substituted $C_1$-$C_6$ alkyl group, a phenethyl group which is optionally substituted on a benzene ring, or an aryloxy group which is optionally substituted on an aromatic ring is more preferred, and a phenethyl group which is optionally substituted on a benzene ring is still more preferred.

The halogen atom represented by $R^{3d}$ and $R^{4d}$ is preferably a fluorine atom or a chlorine atom, and more preferably a chlorine atom.

The optionally substituted $C_1$-$C_6$ alkyl group represented by $R^{3d}$ and $R^{4d}$ is preferably an unsubstituted $C_1$-$C_6$ alkyl group, and more specifically, a methyl group, an ethyl group, an n-propyl group, an isopropyl group, an n-butyl group, a sec-butyl group, an isobutyl group, or a tert-butyl group is preferred, and among them, an isopropyl group or a tert-butyl group is more preferred, and a tert-butyl group is still more preferred.

The $C_3$-$C_6$ cycloalkoxy group represented by $R^{3d}$ and $R^{4d}$ may be a cyclopropyloxy group, a cyclopentyloxy group, or a cyclohexyloxy group, and more preferably a cyclopropyloxy group.

The $C_3$-$C_6$ cycloalkyl group represented by $R^{3d}$ and $R^{4d}$ is preferably a cyclopropyl group, a cyclobutyl group, or a cyclopentyl group, and among them, a cyclopropyl group is more preferred.

The halo $C_1$-$C_4$ alkyl group represented by $R^{3d}$ and $R^{4d}$ is preferably a $C_1$-$C_4$ alkyl group substituted by one or more fluorine atoms, and among them, a $C_1$-$C_4$ alkyl group substituted by 1 to 5 fluorine atoms is more preferred. Specifically, for example, a trifluoromethyl group, a 2,2,2-trifluoroethyl group, a 1,1,2,2-tetrafluoroethyl group, or a pentafluoroethyl group may be included, and among them, a trifluoromethyl group is particularly preferred.

When the optionally substituted ethynyl group represented by $R^{3d}$ and $R^{4d}$ is substituted, the substituent is preferably a $C_1$-$C_6$ alkyl group, a $C_3$-$C_6$ cycloalkyl group or an aryl group, and the aryl group is preferably a phenyl group, and the aryl group may be further substituted by a halogen atom, a $C_1$-$C_6$ alkyl group or a halo $C_1$-$C_4$ alkyl group. The optionally substituted ethynyl group is preferably unsubstituted or preferably has one substituent, and may include, for example, a styryl group, an ethynyl group, a 3-methyl-1-butyn-1-yl group, a cyclopropylethynyl group, a cyclohexylethynyl group, or a phenylethynyl group, and a 3-methyl-1-butyn-1-yl group or a cyclopropylethynyl group is preferred.

The aromatic ring of the aryl group which is optionally substituted on an aromatic ring, or the aryloxy group which is optionally substituted on an aromatic ring, both of which are represented by $R^{3d}$ and $R^{4d}$, is preferably a benzene ring. When the aromatic ring is substituted, the substituent is preferably a halogen atom, a $C_1$-$C_6$ alkyl group, a $C_1$-$C_6$ alkoxy group, or a halo $C_1$-$C_4$ alkyl group. The optionally substituted aryl group or aryloxy group is preferably unsubstituted or preferably has one or two substituents, and more preferably has one substituent at a para position. The optionally substituted aryl group or aryloxy group is specifically, for example, a phenyl group, a 4-trifluoromethylphenyl group, a 4-chlorophenyl group, a 4-tert-butylphenyl group, a 4-methoxyphenyl group, a phenoxy group, a 4-trifluoromethylphenoxy group, a 4-chlorophenoxy group, a 4-tert-butylphenoxy group, or a 4-methoxyphenoxy group, preferably a phenyl group, a 4-trifluoromethylphenyl group, a 4-tert-butylphenyl group, a phenoxy group, a 4-trifluoromethylphenoxy-group, a 4-chlorophenoxy group, or a 4-tertbutylphenoxy group, and more preferably a phenyl group, a phenoxy group, or a 4-chlorophenoxy group.

The benzyl group which is optionally substituted on a benzene ring, the phenethyl group which is optionally substituted on a benzene ring, the benzyloxy group which is optionally substituted on a benzene ring, or the phenyloxymethyl group which is optionally substituted on a benzene ring, all of which are represented by $R^{3d}$ and $R^{4d}$ (hereinafter, the groups from the benzyl group to the phenyloxymethyl group being collectively referred to as the benzyl group and the like of Formula (I-d)) is preferably unsubstituted or preferably has one or two substituents on a benzene ring, and particularly preferably has one substituent at a para position. The substituent is preferably a halogen atom, a $C_1$-$C_6$ alkyl group, or a halo $C_1$-$C_4$ alkyl group, preferably a halogen atom, and most preferably a chlorine atom. The benzyl group and the like of Formula (I-d) are preferably a phenethyl group, or a benzyloxy group, and particularly preferably a phenethyl group. The benzyl group and the like of Formula (I-d) which are optionally substituted on a benzene ring are specifically, for example, a benzyl group, a phenethyl group, a benzyloxy group, a phenyloxymethyl group, a (4-fluoro)phenethyl group, a (4-chloro)phenethyl group, a (4-fluoro)benzyloxy group, a (4-trifluoromethyl) phenethyl group, a (4-trifluoromethyl)benzyloxy group, a (4-tert-butyl)phenethyl group, or a (4-tert-butyl)benzyloxy group, preferably a phenethyl group, a (4-chloro)phenethyl group, a benzyloxy group, or a phenyloxymethyl group, more preferably a phenethyl group, a (4-chloro)phenethyl group, or a benzyloxy group, and still more preferably a phenethyl group or a (4-chloro)phenethyl group.

k is 1 or 2. However, when k is 2, $R^{3d}$ may be different substituents from each other, and also, when k is 2, at least one of $R^{3d}$ is a hydrogen atom or a halogen atom.

k is preferably 1.

The Log D of the compound represented by Formula (I-a), (I-b), (I-c), or (I-d) as an effective component of the medicament of the present invention is, in terms of representing an excellent intraocular pressure lowering action, preferably more than 1.5 and less than 2.5, more preferably 1.6 or more, and still more preferably 1.8 or more, and also, more preferably 2.3 or less, still more preferably 2.2 or less, and particularly preferably 2.1 or less. More specifically, the Log D is more preferably 1.6 or more and 2.3 or less, still more preferably 1.8 or more and 2.2 or less, and particularly preferably 1.8 or more and 2.1 or less. Here, the Log D value in the present invention is a compound partition coefficient between n-octanol and a second solution of a disintegration test of the $16^{th}$ revised Japanese Pharmacopoeia.

A specific example of the compound represented by Formula (I-a) or Formula (I-b), and also having a Log D more than 1.5 and less than 2.5 may include the following compounds:

(−)-4-([N-(4-carboxybutyl)-N-[(2R)-2-(3-cyanophenyl)-2-[4-(2-phenylethyl)benzyloxy]ethyl]amino]methyl)benzoic acid (Compound No. 1), (−)-4-([N-[2-(3-tert-butylbenzyloxy)-(2R)-2-(3-chlorophenyl) ethyl]-N-(4-carboxybutyl)amino]methyl)benzoic acid (Compound No. 2), (−)-4-([N-(4-carboxybutyl)-N-[(2R)-2-[2 fluoro-4-(2-phenylethyl)benzyloxy]-2-phenylethyl]amino]methyl)benzoic acid (Compound No. 3), (−)-4-[(N-(4-carboxybutyl)-N-[(2R)-2-[5-(2-phenylethyl) thiophene-2-ylmethoxy]-2-phenylethyl]amino)methyl]benzoic acid (Compound No. 4), (−)-4-([N-(4-carboxybutyl)-N-[(2R)-2-[4-(4-chlorophenyloxy)benzyloxy]-2-phenylethyl]amino]methyl)benzoic acid (Compound No. 5), (−)-4-([N-(4-carboxybutyl)-N-[(2R)-2-[4-[2-(4-chlorophenyl)ethyl]benzyloxy]-2-phenylethyl]amino]methyl)benzoic acid (Compound No. 6), ([N-(4-carboxybutyl)-N-[2-[4-(2-phenylethyl)benzyloxy]-2-(2-thienyl)ethyl]amino]methyl)benzoic acid (Compound No. 7), (+)-(5S)-5-[N-(4-carboxybutyl)-N-[2-[2-(5,6,7,8-tetrahydronaphthalene-1-ylmethoxy)phenyl]ethyl]amino]-5,6,7,8-tetrahydronaphthalene-2-carboxylic acid (Compound No. 8), (+)-(5S)-5-[N-[2-[2-(3-tert-butylbenzyloxy)phenyl] ethyl]-N-(4-carboxybutyl)amino]-5,6,7,8-tetrahydronaphthalene-2-carboxylic acid (Compound No. 9), (+)-(5S)—[N-(4-carboxybutyl)-N-[2-[2-(4-isopropylbenzyloxy)phenyl]ethyl]amino]-5,6,7,8-tetrahydronaphthalene-2-carboxylic acid (Compound No. 10), (−)-4-([N-(4-carboxybutyl)-N-[(2R)-2-[3-(2-phenylethyl) benzyloxy]-2-phenylethyl]amino]methyl)benzoic acid (Compound No. 11), (−)-1-[N-(4-carboxybutyl)-N-[2-[2-[4-(2-phenylethyl) benzyloxyphenyl]ethyl]amino]indane-5-carboxylic acid (Compound No. 12), 4-([N-(4-carboxybutyl)-N-[2-(4-fluorophenyl)-2-[4-(2-phenylethyl)benzyloxy]ethyl]amino]methyl)benzoic acid (Compound No. 13), (−)-4-([N-(4-carboxybutyl)-N-[(2R)-2-[4-(2-phenylethyl) benzyloxy]-2-phenylethyl]amino]methyl)benzoic acid (Compound No. 14), 5-[N-[2-[2-(2-tert-butylbenzyloxy)phenyl]ethyl]-N-(4-carboxy butyl)amino]-5,6,7,8-tetrahydronaphthalene-2-carboxylic acid (Compound No. 15), 5-[N-(4-carboxybutyl)-N-[2-[2-((2R)-1,2,3,4-tetrahydronaphthalene-2-ylmethoxy)phenyl]ethyl]amino]-5,6,7,8-tetrahydronaphthalene-2-carboxylic acid (Compound No. 16), 5-[N-(4-carboxybutyl)-N-[2-[2-((2S)-1,2,3,4-tetrahydronaphthalene-2-ylmethoxy)phenyl]ethyl]amino]-5,6,7,8-tetrahydronaphthalene-2-carboxylic acid (Compound No. 17), 4-[N-(4-carboxybutyl)-N-[2-[2-(1,2,3,4-tetrahydronaphthalene-6-ylmethoxy)phenyl]ethyl]amino]-chromane-7-carboxylic acid (Compound No. 18), 5-[N-(4-carboxybutyl)-N-[2-[2-(4,5,6,7-tetrahydrobenzo[b]thiophene-2-ylmethoxy)phenyl]ethyl]amino]-5,6,7,8-tetrahydronaphthalene-2-carboxylic acid (Compound No. 19), 5-[N-(4-carboxybutyl)-N-[2-[2-(1,2,3,4-tetrahydronaphthalene-6-ylmethoxy)phenyl]ethyl]amino]-5,6,7,8-tetrahydronaphthalene-2-carboxylic acid (Compound No. 20), 5-[N-(4-carboxybutyl)-N-[2-[2-[4-(2-cyclopropylethynyl)benzyloxy]phenyl]ethyl]amino]-5,6,7,8-tetrahydronaphthalene-2-carboxylic acid (Compound No. 21), 5-[N-(4-carboxybutyl)-N-[2-[2-(4-phenoxymethylbenzyloxy)phenyl]ethyl]amino]-5,6,7,8-tetrahydronaphthalene-2-carboxylic acid (Compound No. 22), (−)-4-([N-(4-carboxybutyl)-N-[(2R)-2-(3-chlorophenyl)-2-[4-(phenyloxy)benzyloxy]ethyl]amino]methyl)benzoic acid (Compound No. 23), 4-[N-[2-[2-(4-benzyloxybenzyloxy)phenyl]ethyl]-N-(4-carboxybutyl)amino]-chromane-7-carboxylic acid (Compound No. 24), 5-[N-[2-[2-(4-tert-butylbenzyloxy)phenyl]ethyl]-N-(4-carboxy butyl)amino]-5,6,7,8-tetrahydronaphthalene-2-carboxylic acid (Compound No. 25), and 5-[N-[2-[2-(4-benzyloxybenzyloxy)phenyl]ethyl]amino-N-(4-carboxybutyl)]-5,6,7,8-tetrahydronaphthalene-2-carboxylic acid (Compound No. 26).

Among the above compounds, the following compounds are more preferred:

(−)-4-([N-(4-carboxybutyl)-N-[(2R)-2-(3-cyanophenyl)-2-[4-(2-phenylethyl)benzyloxy]ethyl]amino]methyl)benzoic acid, (−)-4-([N-(4-carboxybutyl)-N-[(2R)-2-[2-fluoro-4-(2-phenylethyl)benzyloxy]-2-phenylethyl]amino]methyl)benzoic acid, (−)-4-([N-(4-carboxybutyl)-N-[(2R)-2-[4-[2-(4-chlorophenyl)ethyl]benzyloxy]-2-phenylethyl]amino]methyl)benzoic acid, (+)-(5S)-5-[N-(4-carboxybutyl)-N-[(2-[2-(5,6,7,8-tetrahydronaphthalene-1-ylmethoxy)phenyl]ethyl]amino]-5,6,7,8-tetrahydronaphthalene-2-carboxylic acid, (+)(5S)-5-[N-[2-[2-(3-tert-butylbenzyloxy)phenyl]ethyl]-N-(4-carboxybutyl)amino]-5,6,7,8-tetrahydronaphthalene-2-carboxylic acid, (+)-(5S)—[N-(4-carboxybutyl)-N-[2-[2-(4-isopropylbenzyloxy)phenyl]ethyl]amino]-5,6,7,8-tetrahydronaphthalene-2-carboxylic acid, (−)-4-([N-(4-carboxybutyl)-N-[(2R)-2-[3-(2-phenylethyl)benzyloxy]-2-phenylethyl]amino]methyl)benzoic acid, and (−)-4-([N-(4-carboxybutyl)-N-[(2R)-2-[4-(2-phenylethyl)benzyloxy]-2-phenylethyl]amino]methyl)benzoic acid.

In terms of the intraocular pressure lowering action, the following compounds are still more preferred:

(−)-4-([N-(4-carboxybutyl)-N-[(2R)-2-[4-[2-(4-chlorophenyl)ethyl]benzyloxy]-2-phenylethyl]amino]methyl)benzoic acid, (+)-(5S)-5-[N-(4-carboxybutyl)-N-[2-[2-(5,6,7,8-tetrahydronaphthalene-1-ylmethoxy)phenyl]ethyl]amino]-5,6,7,8-tetrahydronaphthalene-2-carboxyl acid, and (−)-4-([N-(4-carboxybutyl)-N-[(2R)-2-[4-(2-phenylethyl)benzyloxy]-2-phenylethyl]amino]methyl)benzoic acid.

In terms of the intraocular pressure lowering action, the following compounds are particularly preferred:

(+)-(5S)-5-[N-(4-carboxybutyl)-N-[2-[2-(5,6,7,8-tetrahydronaphthalene-1-ylmethoxy)phenyl]ethyl]amino]-5,6,7,8-tetrahydronaphthalene-2-carboxylic acid, and (−)-4-([N-(4-carboxybutyl)-N-[(2R)-2-[4-(2-phenylethyl)benzyloxy]-2-phenylethyl]amino]methyl)benzoic acid.

The compound represented by Formula (I-a), (I-b), (I-c), or (I-d), and a pharmaceutically acceptable salt thereof can be prepared according to the method described in Patent Literatures 2 and 3.

The compound represented by Formula (I-a), (I-b), (I-c), or (I-d) having the Log D more than 1.5 and less than 2.5, or a pharmaceutically acceptable salt thereof has an sGC activating effect with excellent heme independency, and as described in the Examples below, has an excellent intraocular pressure lowering action. Therefore, the compound is useful as an ocular hypotensive agent or a therapeutic agent for glaucoma in an animal including a human being.

The medicament of the present invention can be administered orally or parenterally. A dosage of the compound of Formula (I-a) or (I-b) is appropriately determined depending on each case, considering for example, the age, body weight or sex of subject to whom the medicament is to be administered. Usually, in the case of oral administration, the dosage of the compound per day for an adult (a body weight of about 60 kg) is 1 to 1000 mg, preferably 3 to 300 mg, and more preferably 10 to 200 mg, which is administered in one dose, or in two to four divided doses. In addition, in the case of intravenous administration, the daily dosage for an adult is 0.01 to 100 mg, preferably 0.01 to 50 mg, and more preferably 0.01 to 20 mg, per 1 kg of a body weight, which is administered in one dose, or in multiple divided doses per day. In addition, in the case of administration by instillation, the concentration of the effective component of 0.001 to 10 w/v %, preferably 0.005 to 5 w/v %, and more preferably 0.01 to 1 w/v % is administered in one dose or multiple divided doses per day for an adult.

The pharmaceutical composition of the present invention can be prepared by a common method, using one or more of the compound and a pharmaceutically acceptable additive.

The pharmaceutical composition of the present invention for oral administration may include, for example, a tablet, a pill, a capsule, a granule, a powder, an emulsion, a solution, a suspension, a syrup, or an elixir. These may be prepared as a pharmaceutical composition in which one or more of the compound of the present invention, and a pharmaceutically acceptable diluent, excipient, or carrier are mixed. In addition, the composition may include an additive such as a binder, a disintegrating agent, a lubricant, a swelling agent, a swelling aid, a coating agent, a plasticizer, a stabilizer, an antisepsis, an antioxidant, a coloring agent, a dissolution aid, a suspending agent, an emulsifying agent, a sweetening agent, a preservative, a buffer, and a wetting agent.

The pharmaceutical composition of the present invention for parenteral administration may include for example, an injection, a suppository, an eye drop, an inhalant, an ointment, a gel, a cream, or a patch. Among them, particularly an eye drop is preferred. These may be prepared into a pharmaceutical composition in which one or more of the compound of the present invention and an additive such as pharmaceutically acceptable diluent, excipient, and carrier. In addition, the composition may include an additive such as a stabilizer, an antisepsis, a dissolution aid, a humectant, a preservative, an antioxidant, a flavoring agent, a gelling agent, a neutralizing agent, a buffer, an isotonicity agent, a surfactant, a coloring agent, a buffering agent, a thickening agent, a wetting agent, a filler, an absorption accelerator, a suspending agent, and a binder.

As the eye drop, any one of, for example, an aqueous eye drop, a non-aqueous eye drop, a suspended eye drop, an emulsion eye drop or an eye ointment may be used.

For example, when the eye drop is prepared, in the compound represented by Formula (I-a), (I-b), (I-c), or (I-d) having the Log D more than 1.5 and less than 2.5 or a pharmaceutically acceptable salt thereof, if necessary, for example, an isotonizing agent such as sodium chloride and glycerin; a stabilizer such as sodium edetate; an antisepsis such as benzalkonium chloride and parabens; or a pH adjusting agent such as sodium hydrogen phosphate, sodium dihydrogen phosphate, boric acid, sodium tetraborate (borax), hydrochloric acid, and sodium hydroxide is used to prepare the eye drop, by a common method.

EXAMPLES

Hereinafter, the present invention is specifically described by referring to the Examples, however, the present invention shall not be limited to these embodiments.

Example 1

(Determination of Log D Value)

The Log D value was determined using a flask shaking method, where a test compound partition coefficient between n-octanol and the second solution for the disintegration test defined in the $16^{th}$ revised Japanese Pharmacopoeia was calculated. Specifically, in a microtube containing 2 mg of the test compound, n-octanol (0.25 mL) and the second solution for the disintegration test (0.25 mL) were mixed. The tube was shaken in a multi shaker at room temperature for 60 minutes, and allowed to stand until the two phases were completely separated. In the microtube, 10 μL of an n-octanol phase was diluted with 190 μL of 85% methanol and mixed, thereby obtaining an organic phase test solution. 100 μL of the second solution phase for the disintegration test was diluted with 100 μL of 50% methanol, and mixed, thereby obtaining an aqueous phase test solution. The organic phase test solution and the aqueous phase test solution were filtered, respectively, and the concentration of the test compound in these test solutions were measured, using high performance liquid chromatography. Then, from the measured concentration and dilution rate, the Log D was calculated.

That is, the Log D of the present specification is represented by the following equation:

Log $D$=Log$_{10}$([concentration of test compound in organic phase test solution]/[concentration of test compound in aqueous phase test solution])+1     [Equation 1]

The second solution for the disintegration test herein refers to, as defined in the 16th revised Japanese Pharmacopoeia, a liquid obtained by adding to 250 mL of a 0.2 mol/L potassium dihydrogenphosphate reagent, 118 mL of a 0.2 mol/L sodium hydroxide reagent, and water for adjusting to 1000 mL volume.

Example 2

(Measurement of sGC Activating Effect)

Chinese Hamster ovary cells (CHO-K1 cells) modified for stably expressing human sGC α subunit and β subunit, and a mouse cyclic nucleotide gated channel (CNGA2) were used in the test.

The CHO-K1 cells stably expressing human sGC and mouse CNGA2 were cultured at 37° C. in a F-12 medium supplemented with 10% (v/v) fetal bovine serum (FBS), penicillin (100 U/mL), streptomycin (100 μg/mL), G418 (250 μg/mL), and Zeocin (250 μg/mL). The cells were suspended in a culture medium, seeded in a 96 well plate, and cultured at 37° C. for 24 hours. The cells were washed with an assay buffer 1 (140 mmol/L of sodium chloride, 5 mmol/L of potassium chloride, 0.5 mmol/L of magnesium chloride, 0.01 mmol/L of calcium chloride, 10 mmol/L of glucose, 0.4 mmol/L of magnesium sulfate, 10 mmol/L of 4-(2-hydroxyethyl)piperazine-1-yl ethanesulfonic acid, 125 μmol/L of sulfinpyrazone, pH 7.4), and then an indicator solution in which Fura2-AM as a fluorescent Ca2+ indicator is dissolved in assay buffer 1 at a concentration of 5 μmol/L was added thereto, and cultured at 37° C. for 60 minutes. The culture medium was removed, the cells were washed with assay buffer 1, the test compound solution was added thereto, and cultured at room temperature for 10 minutes. The plate was mounted on a fluorescence microplate reader (FlexStation II, available from Molecular Devices) with setting of excitation wavelengths of 340 and 380 nm and a detection wavelength of 510 nm, an intracellular calcium concentration was measured as a fluorescent intensity ratio obtained from each excitation wavelength.

In this test, the solution of the test compound was prepared by dissolving each test compound in DMSO at a concentration of 10 mmol/L, and then diluting the solution with assay buffer 2 (140 mmol/L of sodium chloride, 5 mmol/L of potassium chloride, 0.5 mmol/L of magnesium chloride, 1 mmol/L of calcium chloride, 10 mmol/L of glucose, 0.4 mmol/L of magnesium sulfate, 10 mmol/L of 4-(2-hydroxyethyl)piperazine-1-yl ethanesulfonic acid, 125 μmol/L of sulfinpyrazone, 100 μmol/L of isobutylmethylxanthine, 10 μmol/L of 1H-[1,2,4]-oxadiazole [4,3-a]quinoxaline-1-on (hereinafter, referred to as ODQ), pH 7.4), in order to adjust the concentration of 10 μmol/L for testing. As a control solution, a DMSO diluted solution was used, instead of the test compound solution.

The activity of the test compound was calculated as an increase rate (%) of the sGC activity in the test compound solution relative to the sGC activity in the control solution, by dividing a fluorescent intensity ratio in adding the test compound by a fluorescent intensity ratio of the control solution, and subtracting the sGC activity in the control solution (100%) therefrom. An EC$_{50}$ value was calculated from the activity of the test compound at concentrations of 0.0001, 0.001, 0.003, 0.01, 0.03, 0.1, 1, and 10 μmol/L, using a 4 parameter losgistic model from Assay Explorer (available from Dssault Systèmes BIOVIA).

Hereinafter, the results of measuring Log D and EC$_{50}$ are shown in Tables 1 to 8.

TABLE 1

| Compound No. | Structural formula | LogD | EC50 (nM) |
|---|---|---|---|
| 1 | 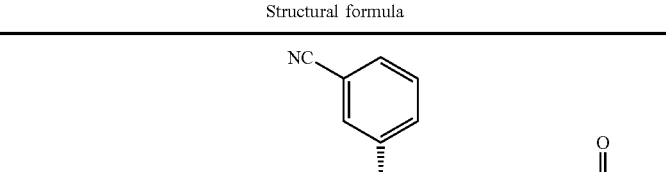 | 2.03 | 8.80 |

TABLE 1-continued
| Compound No. | Structural formula | LogD | EC50 (nM) |
|---|---|---|---|
| 2 | 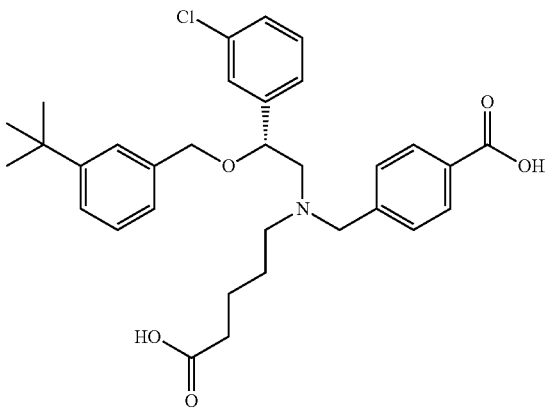 [SMILES: CC(C)(C)c1cccc(CO[C@@H](CN(CCCCC(=O)O)Cc2ccc(C(=O)O)cc2)c2cccc(Cl)c2)c1] | 2.14 | 1.54 |
| 3 | 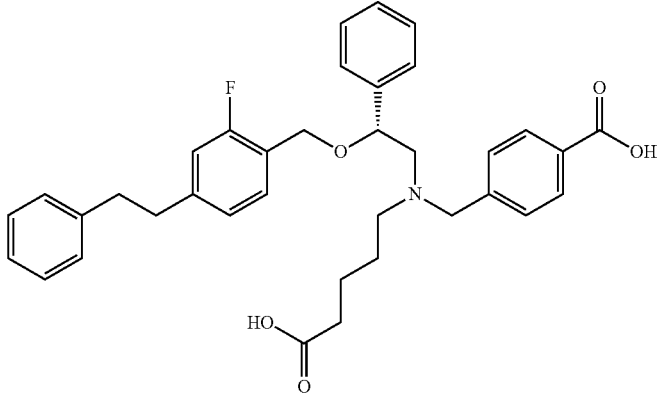 [SMILES: O=C(O)CCCCN(Cc1ccc(C(=O)O)cc1)C[C@H](OCc1ccc(CCc2ccccc2)cc1F)c1ccccc1] | 1.99 | 2.35 |
| 4 | 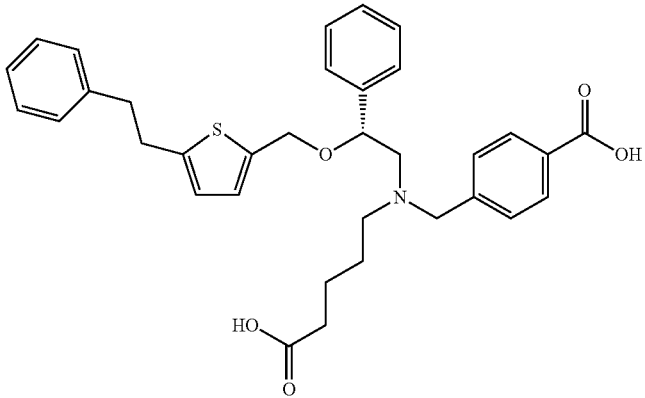 [SMILES: O=C(O)CCCCN(Cc1ccc(C(=O)O)cc1)C[C@H](OCc1ccc(CCc2ccccc2)s1)c1ccccc1] | 1.80 | 1.61 |

TABLE 2

| Compound No. | Structural formula | LogD | EC50 (nM) |
|---|---|---|---|
| 5 | | 2.17 | 6.49 |
| 6 | | 2.02 | 3.14 |
| 7 | | 2.11 | 3.92 |
| 8 | | 1.87 | 6.62 |

TABLE 3

| Compound No. | Structural formula | LogD | EC50 (nM) |
|---|---|---|---|
| 9 | | 2.09 | 7.09 |
| 10 | | 1.88 | 9.63 |
| 11 | | 1.94 | 1.99 |
| 12 | | 1.95 | 11.88 |

TABLE 4
| Compound No. | Structural formula | LogD | EC50 (nM) |
|---|---|---|---|
| 13 | 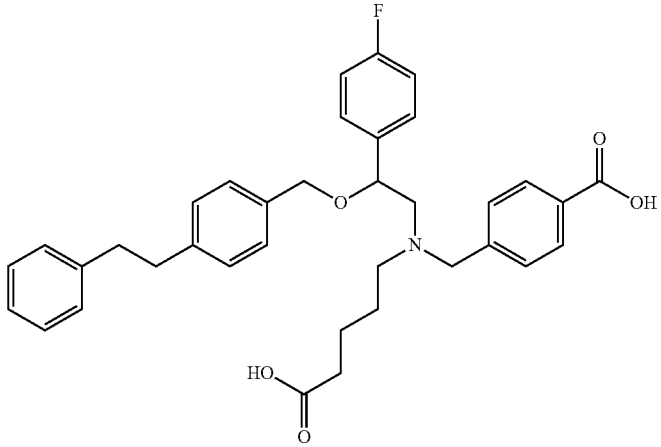 [SMILES: O=C(O)CCCCN(Cc1ccc(C(=O)O)cc1)CC(OCc1ccc(CCc2ccccc2)cc1)c1ccc(F)cc1] | 2.19 | 26.46 |
| 14 | 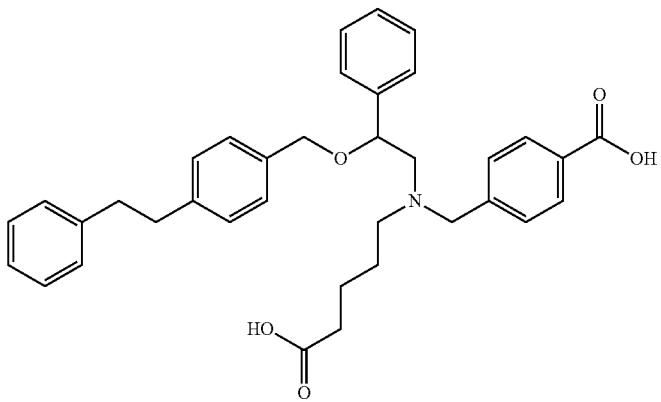 [SMILES: O=C(O)CCCCN(Cc1ccc(C(=O)O)cc1)CC(OCc1ccc(CCc2ccccc2)cc1)c1ccccc1] | 2.04 | 5.71 |
| 15 | 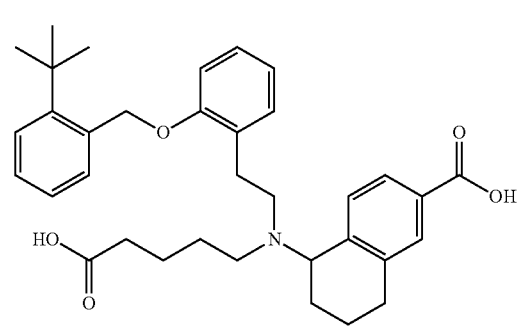 [SMILES: CC(C)(C)c1ccccc1COc1ccccc1CCN(CCCCC(=O)O)C1CCCc2cc(C(=O)O)ccc21] | 1.95 | 13.44 |
| 16 | 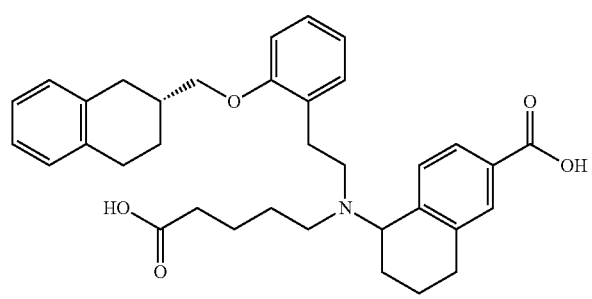 [SMILES: O=C(O)CCCCN(CCc1ccccc1OC[C@@H]1CCc2ccccc2C1)C1CCCc2cc(C(=O)O)ccc21] | 1.99 | 7.50 |

TABLE 5
| Compound No. | Structural formula | LogD | EC50 (nM) |
|---|---|---|---|
| 17 | 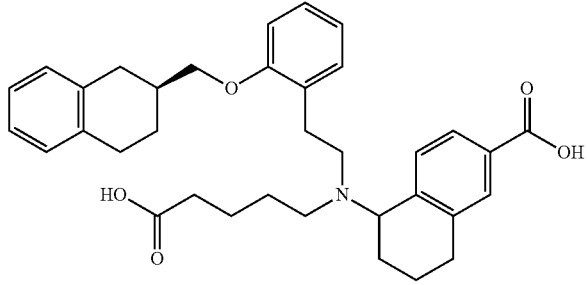 [SMILES: O=C(O)CCCCN(CCc1ccccc1OC[C@H]1CCc2ccccc2C1)C1CCCc2cc(C(=O)O)ccc21] | 2.00 | 10.98 |
| 18 | 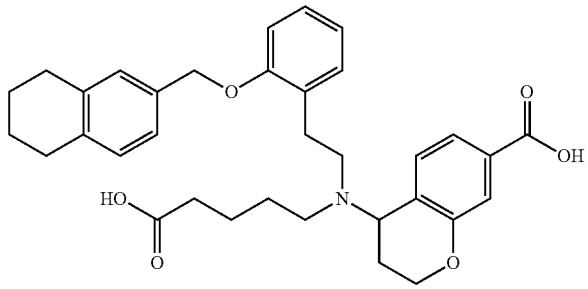 [SMILES: O=C(O)CCCCN(CCc1ccccc1OCc1ccc2c(c1)CCCC2)C1CCOc2cc(C(=O)O)ccc21] | 2.14 | 2.90 |
| 19 | 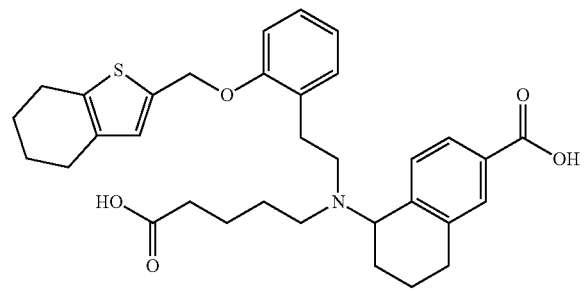 [SMILES: O=C(O)CCCCN(CCc1ccccc1OCc1cc2c(s1)CCCC2)C1CCCc2cc(C(=O)O)ccc21] | 1.74 | 33.50 |
| 20 | 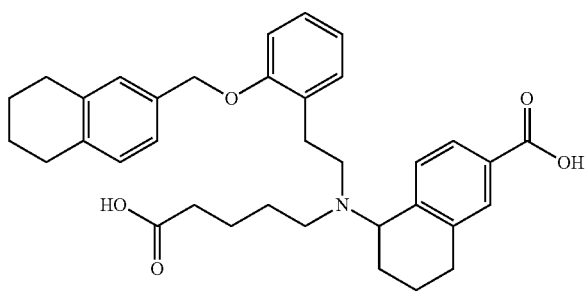 [SMILES: O=C(O)CCCCN(CCc1ccccc1OCc1ccc2c(c1)CCCC2)C1CCCc2cc(C(=O)O)ccc21] | 1.87 | 3.96 |

TABLE 6
| Compound No. | Structural formula | LogD | EC50 (nM) |
|---|---|---|---|
| 21 | 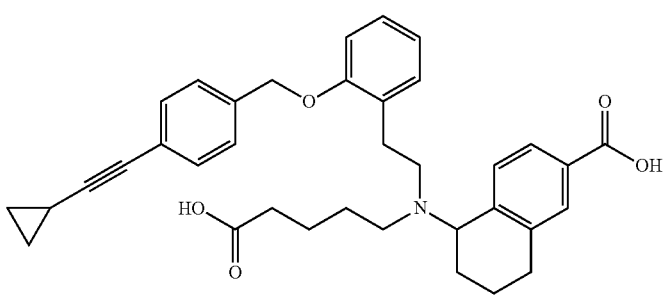 [SMILES: O=C(O)CCCCN(CCc1ccccc1OCc1ccc(C#CC2CC2)cc1)C1CCCc2cc(C(=O)O)ccc21] | 2.06 | 15.93 |
| 22 | 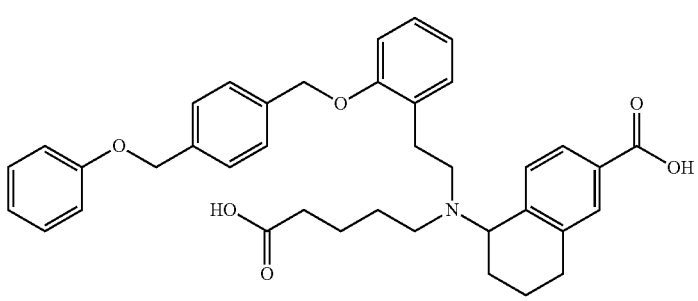 [SMILES: O=C(O)CCCCN(CCc1ccccc1OCc1ccc(COc2ccccc2)cc1)C1CCCc2cc(C(=O)O)ccc21] | 2.18 | 8.86 |
| 23 | 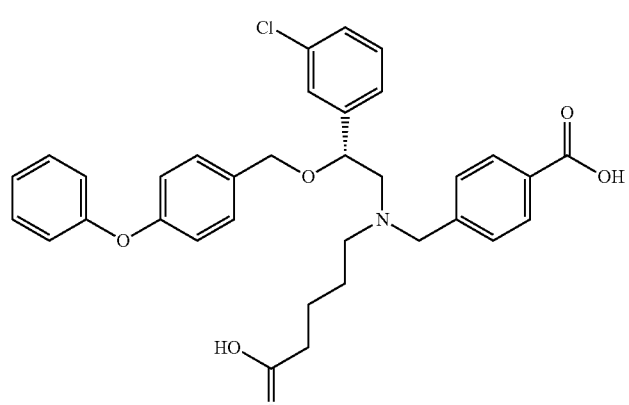 | 2.35 | 2.47 |
| 24 | 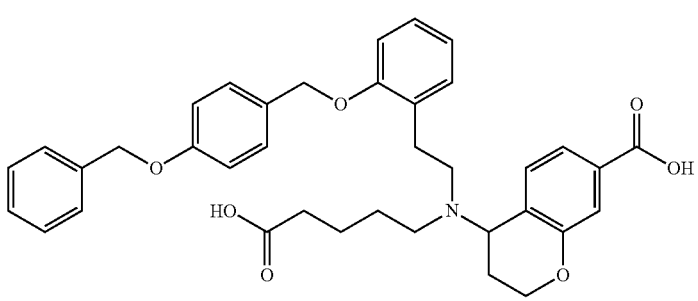 | 2.40 | 8.73 |

TABLE 7
| Compound No. | Structural formula | LogD | EC50 (nM) |
|---|---|---|---|
| 25 | 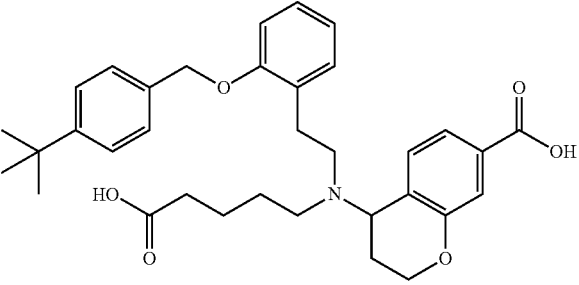 [SMILES: CC(C)(C)c1ccc(COc2ccccc2CCN(CCCCC(=O)O)C2CCOc3cc(C(=O)O)ccc32)cc1] | 2.25 | 4.43 |
| 26 | 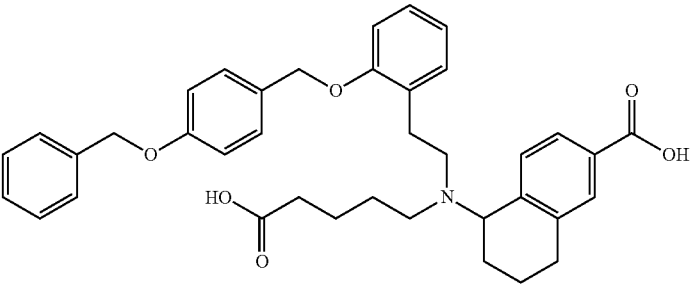 [SMILES: O=C(O)CCCCN(CCc1ccccc1OCc1ccc(OCc2ccccc2)cc1)C1CCCc2cc(C(=O)O)ccc21] | 2.24 | 15.59 |
| Comparative Compound 1 | 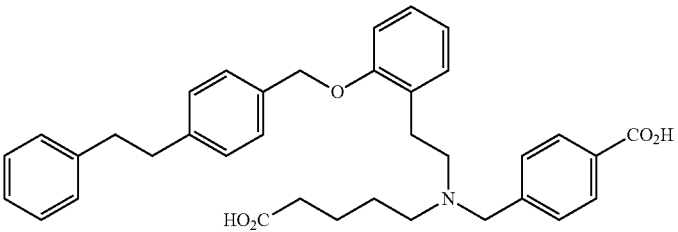 [SMILES: O=C(O)CCCCN(CCc1ccccc1OCc1ccc(CCc2ccccc2)cc1)Cc1ccc(C(=O)O)cc1] | 1.50 | 8.84 |
| Comparative Compound 2 | 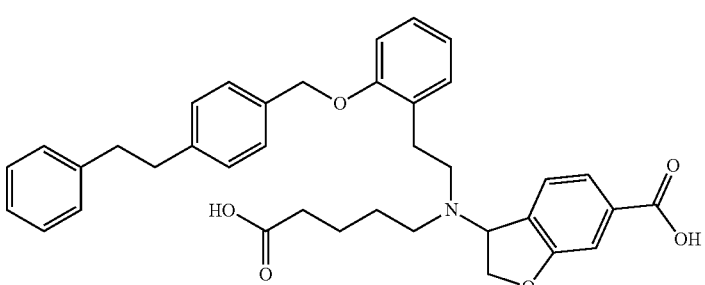 | 2.59 | 19.45 |

TABLE 8

| Compound No. | Structural formula | LogD | EC50 (nM) |
|---|---|---|---|
| Comparative Compound 3 | 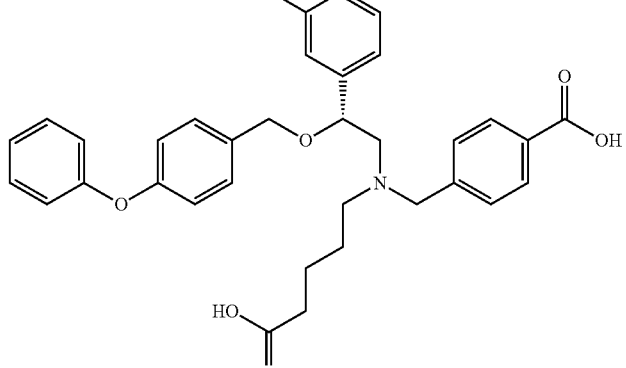 | 1.32 | 7.01 |
| Comparative Compound 4 | 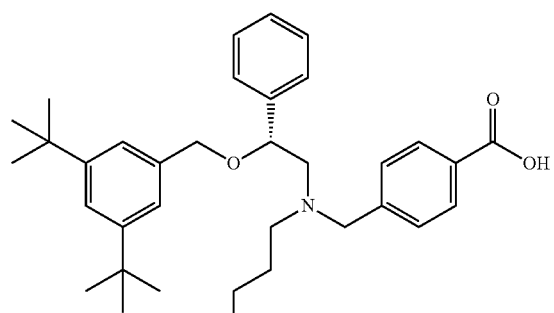 | 2.78 | 0.46 |

Example 3

Evaluation of Influence on Intraocular Pressure in Rabbits with Normal Intraocular Pressure (Experimental Animal)

Rabbits (strain: Std:NZW, sex: male) with normal intraocular pressure were acclimated to breeding environment for more than three weeks, and subjected to test (three rabbits per one group).

(Sample Preparation)

A test compound was weighed, and a required amount of a 10 mmol/L or 20 mmol/L tris hydrochloric acid buffer solution was added thereto with a micropipette and dissolved therein. If necessary, a 1 mol/L hydrochloric acid or a 1 mol/L sodium hydroxide solution was used to prepare a physiological pH, to obtain the test compound solution (0.1 w/v % solution).

(Test Method)

50 µL of the test compound solution was instilled into one eye, and 50 µL of a saline solution was instilled into the other eye as a negative control. Three hours after administration, intraocular pressure was measured. In addition, the measurement of intraocular pressure was repeated in the manner of right eye→left eye→right eye→left eye→ . . . , and continued until the changes of three consecutive intraocular pressures of the right eye and the left eye were within 1 mmHg, respectively. The average of three intraocular pressures at that time was recorded as the intraocular pressure at that time. In addition, ΔIOP (mmHg) was calculated by subtracting the intraocular pressure of the eye for instillation of the test compound solution from the intraocular pressure of the eye for instillation of the saline solution.

(Test Result)

The test results are shown in Table 9. In addition, the data represents an average of three tests per one group.

TABLE 9

| Compound No. | LogD | ΔIOP (mmHg) |
|---|---|---|
| 6 | 2.02 | 3.4 |
| 8 | 1.87 | 5.2 |
| 14 | 2.04 | 5.0 |
| Comparative Compound 1 | 1.50 | 0.3 |
| Comparative Compound 2 | 2.59 | 1.5 |
| Comparative Compound 3 | 1.32 | 1.1 |
| Comparative Compound 4 | 2.78 | 0.2 |

The invention claimed is:

1. A method of treating glaucoma or lowering intraocular pressure, comprising administering, to a subject in need thereof, an effective amount of a compound represented by Formula (I-a) or Formula (I-b) having a Log D value of more than 1.5 and less than 2.5, or a pharmaceutically acceptable salt thereof:

(I-a)

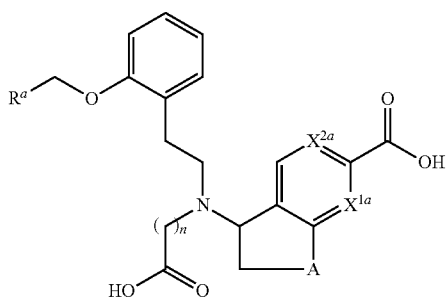

(I-b)

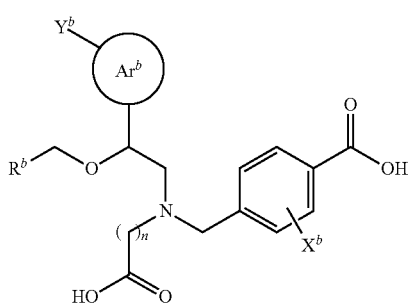

wherein A is a $C_1$-$C_3$ alkylene chain, in which one methylene group is optionally substituted by an oxygen atom or a sulfur atom;

$R^a$ is a group selected from the group consisting of formulae:

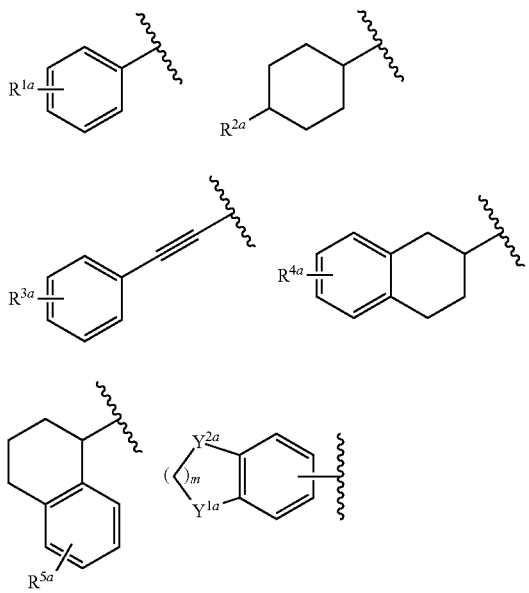

$R^b$ is a group selected from the group consisting of formulae:

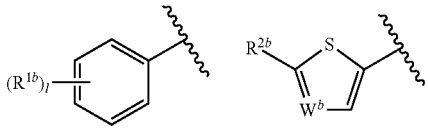

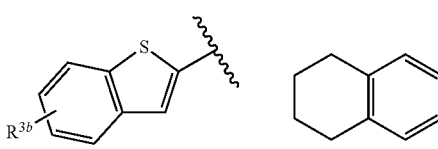

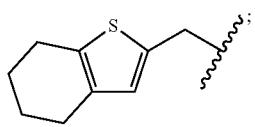

$R^{1a}$, $R^{2a}$, $R^{3a}$, $R^4$, $R^{5a}$, $R^{1b}$, $R^{2b}$, and $R^{3b}$ are independently from each other a hydrogen atom, a halogen atom, an optionally substituted $C_1$-$C_6$ alkyl group, a $C_1$-$C_6$ alkoxy group, a $C_3$-$C_6$ cycloalkyl group, a $C_3$-$C_6$ cycloalkoxy group, a halo $C_1$-$C_4$ alkyl group, an optionally substituted ethynyl group, an aryl group which is optionally substituted on an aromatic ring, an aryloxy group which is optionally substituted on an aromatic ring, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring;

$Ar^b$ is an aryl group, or a heteroaryl group of a 5- or 6-membered ring comprising a nitrogen atom, an oxygen atom, or a sulfur atom:

$X^{1a}$ and $X^{2a}$ are independently from each other CH or a nitrogen atom;

$X^b$ is a hydrogen atom or a halogen atom;

$Y^{1a}$ and $Y^{2a}$ are independently from each other methylene, an oxygen atom, or a sulfur atom, but both of $Y^{1a}$ and $Y^{2a}$ are not a sulfur atom:

$Y^b$ is a hydrogen atom, a $C_1$-$C_6$ alkyl group, a halo $C_1$-$C_4$ alkyl group, a cyano group, or a halogen atom;

$W^b$ is CH or a nitrogen atom;

l is an integer of 1 to 3, and when l is 2 or more, $R^{1b}$ may be different from each other:

m is 1 or 2; and n is an integer of 3 to 5.

2. The method of claim 1, wherein the compound represented by Formula (I-a) or Formula (I-b) has the Log D value of 1.6 or more and 2.3 or less.

3. The method of claim 1, wherein the compound represented by Formula (I-a) or Formula (I-b) has the Log D value of 1.8 or more and 2.2 or less.

4. The method of claim 1, wherein the compound represented by Formula (1-a) or Formula (1-b) has the Log D value of 1.8 or more and 2.1 or less.

5. The method of claim 1, wherein the compound represented by Formula (I-a) or Formula (I-b) is a compound represented by Formula (I-c) or Formula (I-d):

(I-c)

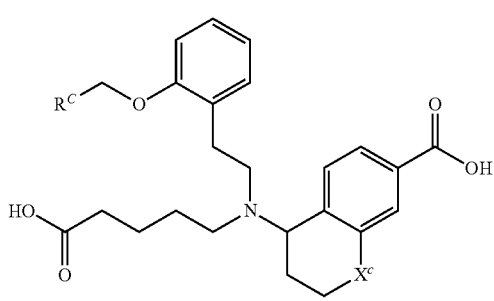

wherein $X^c$ is a methylene group, a single bond or an oxygen atom; and $R^C$ is a group selected from the group consisting of formulae:

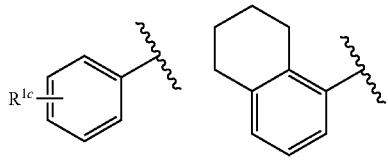

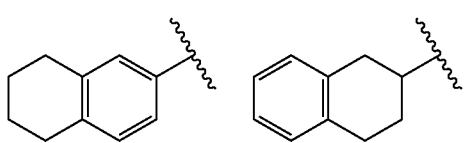

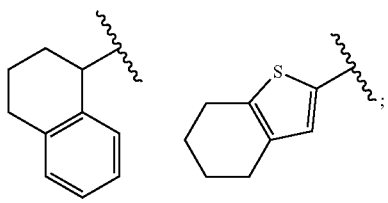

$R^{1c}$ is a hydrogen atom, a halogen atom, an optionally substituted $C_1$-$C_6$ alkyl group, a $C_1$-$C_6$ alkoxy group, a $C_3$-$C_6$ cycloalkyl group, a $C_3$-$C_6$ cycloalkoxy group, a halo $C_1$-$C_4$ alkyl group, an optionally substituted ethynyl group, an aryl group which is optionally substituted on an aromatic ring, an aryloxy group which is optionally substituted on an aromatic ring, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted a benzene ring;

(1-d)

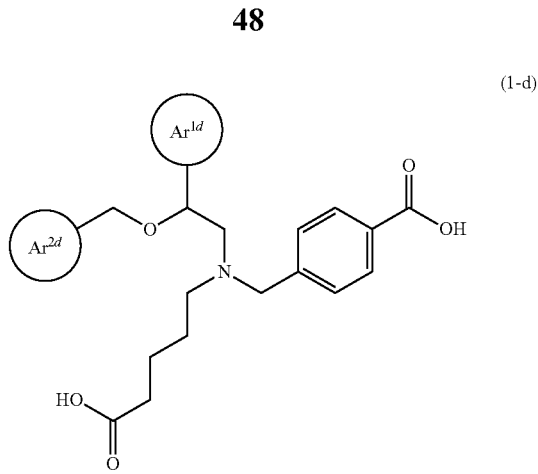

wherein $Ar^{1d}$ is a group selected from the group consisting of formulae:

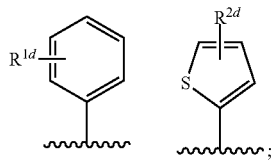

$Ar^2$ is a group selected from the group consisting of formulae:

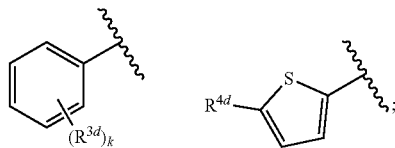

$R^{1d}$ and $R^{2d}$ are a hydrogen atom, a $C_1$-$C_6$ alkyl group, a halo $C_1$-$C_4$ alkyl group, a cyano group, or a halogen atom;

$R^{3d}$ and $R^{4d}$ are a hydrogen atom, a halogen atom, an optionally substituted $C_1$-$C_6$ alkyl group, a $C_1$-$C_6$ alkoxy group, a $C_3$-$C_6$ cycloalkyl group, a $C_3$-$C_6$ cycloalkoxy group, a halo $C_1$-$C_4$ alkyl group, an optionally substituted ethynyl group, an aryl group which is optionally substituted an aromatic ring, an aryloxy group which is optionally substituted on an aromatic ring, a benzyl group which is optionally substituted on a benzene ring, a phenethyl group which is optionally substituted on a benzene ring, a benzyloxy group which is optionally substituted on a benzene ring, or a phenyloxymethyl group which is optionally substituted on a benzene ring, but when $R^{1d}$ or $R^{2d}$ is a cyano group, $R^{3d}$ is not an aryloxy group which is optionally substituted on an aromatic ring; and k is 1 or 2, but when k is 2, $R^{3d}$ may be different substituents from each other, and when k is 2, at least one of $R^{3d}$ is a hydrogen atom or a halogen atom.

6. The method of claim 1, wherein the compound represented by Formula (I-a) or Formula (I-b) is at least one selected from the group consisting of:

(−)-4-([N-(4-carboxybutyl)-N-[(2R)-2-(3-cyanophenyl)-2-[4-(2-phenylethyl)benzyloxy]ethyl]amino]methyl)benzoic acid, (−)-4-([N-[2-(3-tert-butylbenzyloxy)-(2R)-2-(3-chlorophenyl)ethyl]-N-(4-carboxybutyl)amino]methyl)benzoic acid, (−)-4-([N-(4-carboxybutyl)-N-[(2R)-2-[2-fluoro-4-(2-phenylethyl)benzyloxy]-2-phenylethyl]amino]methyl)benzoic acid, (−)-4-[(N-(4-carboxybutyl)-N-[(2R)-2-[5-(2-phenylethyl)thiophene-2-ylmethoxy]-2-phenylethyl]amino)methyl]benzoic acid, (−)-4-([N-(4-carboxybutyl)-N-[(2R)-2-[4-(4-chlorophenyloxy)benzyloxy]-2-phenylethyl]amino]methyl)benzoic acid, (−)-4-([N-(4-carboxybutyl)-N-[(2R)-2-[4-[2-(4-chlorophenyl)ethyl]benzyloxy]-2-phenylethyl]amino]methyl)benzoic acid, 4-([N-(4-carboxybutyl)-N-[2-[4-(2-phenylethyl)benzyloxy]-2-(2-thienyl)ethyl]amino]methyl)benzoic acid, (+)-(5S)-5-[N-(4-carboxybutyl)-N-[2-[2-(5,6,7,8-tetrahydronaphthalene-1-ylmethoxy)phenyl]ethyl]amino]-5,6,7,8-tetrahydronaphthalene-2-carboxylic acid, (+)-(5S)-5-[N-[2-[2-(3-tert-butylbenzyloxy)phenyl]ethyl]-N-(4-carboxybutyl)amino]-5,6,7,8-tetrahydronaphthalene-2-carboxylic acid, (+)-(5 S)—[N-(4-carboxybutyl)-N-[2-[2-(4-isopropylbenzyloxy)phenyl]ethyl]amino]-5,6,7,8-tetrahydronaphthalene-2-carboxylic acid, (−)-4-([N-(4-carboxybutyl)-N-[(2R)-2-[3-(2-phenylethyl)benzyloxy]-2-phenylethyl]amino]methyl)benzoic acid, (−)-1-[N-(4-carboxybutyl)-N-[2-[2-[4-(2-phenylethyl)benzyloxyphenyl]ethyl]amino]indane-5-carboxylic acid, 4-([N-(4-carboxybutyl)-N-[2-(4-fluorophenyl)-2-[4-(2-phenylethyl)benzyloxy]ethyl]amino]methyl)benzoic acid, (−)-4-([N-(4-carboxybutyl)-N-[(2R)-2-[4-(2-phenylethyl)benzyloxy]-2-phenylethyl]amino]methyl)benzoic acid, 5-[N-[2-[2-(2-tert-butylbenzyloxy)phenyl]ethyl]-N-(4-carboxybutyl)amino 1-5,6,7,8-tetrahydronaphthalene-2-carboxylic acid, 5-[N-(4-carboxybutyl)-N-[2-[2-((2R)-1,2,3,4-tetrahydronaphthalene-2-ylmethoxy)phenyl]ethyl]amino]-5,6,7,8-tetrahydronaphthalene-2-carboxylic acid, 5-[N-(4-carboxybutyl)-N-[2-[2-((2S)-1,2,3,4-tetrahydronaphthalene-2-ylmethoxy)phenyl]ethyl]amino]-5,6,7,8-tetrahydronaphthalene-2-carboxylic acid, 4-[N-(4-carboxybutyl)-N-12-12-(1,2,3,4-tetrahydronaphthalene-6-ylmethoxy)phenyl]ethyl]amino]-chromane-7-carboxylic acid, 5-[N-(4-carboxybutyl)-N-[2-[2-(4,5,6,7-tetrahydrobenzo[b]thiophene-2-ylmethoxy)phenyl]ethyl]amino]-5,6,7,8-tetrahydronaphthalene-2-carboxylic acid, 5-[N-(4-carboxybutyl)-N-[2-[2-(1,2,3,4-tetrahydronaphthalene-6-ylmethoxy)phenyl]ethyl]amino]-5,6,7,8-tetrahydronaphthalene-2-carboxylic acid, 5-[N-(4-carboxybutyl)-N-[2-[2-[4-(2-cyclopropylethynyl)benzyloxy]phenyl]ethyl]amino]-5,6,8-tetrahydronaphthalene-2-carboxylic acid, 5-[N-(4-carboxybutyl)-N-[2-[2-(4-phenoxymethylbenzyloxy)phenyl]ethyl]amino]-5,6,7,8-tetrahydronaphthalene-2-carboxylic acid, (−)-4-([N-(4-carboxybutyl)-N-[(2R)-2-(3-chlorophenyl)-2-[4-(phenyloxy)benzyloxy]ethyl]amino]methyl)benzoic acid, 4-[N-[2-[2-(4-benzyloxybenzyloxy)phenyl]ethyl]-N-(4-carboxybutyl)amino]-chromane-7-carboxylic acid, 5-[N-[2-[2-(4-tert-butylbenzyloxy)phenyl]ethyl]-N-(4-carboxybutyl)aminol-5,6,7,8-tetrahydronaphthalene-2-carboxylic acid, and 5-[N-[2-[2-(4-benzyloxybenzyloxy)phenyl]ethyl]amino-N-(4-carboxybutyl)-]-5,6,7,8-tetrahydronaphthalene-2-carboxylic acid.

\* \* \* \* \*